(12) United States Patent
Kenten et al.

(10) Patent No.: US 6,218,519 B1
(45) Date of Patent: Apr. 17, 2001

(54) COMPOUNDS AND METHODS FOR THE SELECTIVE TREATMENT OF CANCER AND BACTERIAL INFECTIONS

(75) Inventors: John H. Kenten, Boyds; David M. Simpson, N. Bethesda, both of MD (US)

(73) Assignee: Pro-Neuron, Inc., Rockville, MD (US)

( * ) Notice: Subject to any disclaimer, the term of this patent is extended or adjusted under 35 U.S.C. 154(b) by 0 days.

(21) Appl. No.: 08/635,243

(22) Filed: Apr. 12, 1996

(51) Int. Cl.$^7$ ...................................................... C07H 15/24
(52) U.S. Cl. ............................................. 536/6.4; 549/424
(58) Field of Search ............................. 549/424; 536/6.4

(56) References Cited

U.S. PATENT DOCUMENTS

| | | | |
|---|---|---|---|
| 4,327,074 | 4/1982 | Rubin et al. | 424/1.5 |
| 4,337,760 | 7/1982 | Rubin | 128/1 R |
| 5,196,522 | 3/1993 | Farquhar et al. | 536/6.4 |

OTHER PUBLICATIONS

Tietze, L.F., et al, *Liebigs Ann. Chem.*, 565–577 (1988), "Synthesis of Glycoconjugates of Acetal–glycosides with Lysine and Tripeptides for Selective Cancer Therapy".
Tietz, L.F., et al, *Liebigs Ann. Chem.*, 151–157 (1990), "Novel Stable Bioactivated Cyclophosphamide Derivatives for Selective Cancer Chemotherapy, Synthesis of Aldophosphamide Acetal–glycosides and Their Glycoconjugates".
Andrianomenjanahary, S., et al, *Organic & Medicinal Chemistry Letters*, vol. 2, No. 9, pp. 1093–1096, 1992, "Synthesis of Novel Targeted Pro–Prodrugs of Anthracyclines Potentially Activated by a Monoclonal Antibody Galactosidase Conjugate (Part 1)".
Abdallah, C., et al, *J. Med. Chem.*, 35, 3208–3214 (1992), "N–(5,5–Diacetoxypent–1–yl)doxorubicin: A New Intensely Potent jDoxorubicin Analogue".
Acton, E.M., et al, *J. Med. Chem.*, 27, 638–645 (1984) "Intensely Potent Morpholinyl Anthracyclines".
Lal, R.B., et al, *Journal of Immunological Methods*, 79, 307–318 (1985), "Selective Elimination of Lymphocyte Subpopulations by Monoclonal Antibody–Enzyme Conjugates".
Tietze, L.F., et al, *Carbohydrate Research*, 148, 349–352 (1986), "Stereoselective synthesis of I–O–trimethylsilyl–α– and –β–D–glucopyranuronate".
Ruben, G.G., et al, *Tetrahedron Letters*, vol. 36, No. 10, pp. 1701–1704, 1995, "β–Glucuronyl Carbamate Based Pro–moieties Designed for Produrgs in ADEPT".
Kaneko, T., et al, *Bioconjugate Chemistry*, vol. 2, No. 3, pp. 133–141, May/Jun. 1991, "New Hydrazone Derivatives of Adriamycin and Their Immunoconjugates—a Correlation between Acid Stability and Cytotoxicity".
Streeter, D.G., al, *Cancer Chemother. Pharmacol.*, 1:160–164 (1985), "Comparative cytotoxicities of various morpholinyl anthracyclines".

Tannock, I.F., et al, *Cancer Research*, 49:4373–4384, Aug. 15, 1989 "Acid pH in tumors and Its Potential for Therapeutic Exploitation".
*The Journal of Antibiotics*, vol. XLI, No. 3, pp. 404–408, Mar. 1988, Communications to the Editor, "New Potent Anthracyclines, Barminomycins I and II".
Connors, T.A., et al, *Biochemical Pharmacology*, vol. 13, pp. 395–400, 1964, Pergamon Press Ltd., Printed in Great Britain, "The Effect of Glucose Pretreatment of the Carcinostatic and Toxic activities of some Alkylating Agents".
Tietze, L.F., et al, *Carbohydrate Research*, 164:177–194 (1987), "Synthesis of Acetal–α–Glucosides, A Stereoselective Entry into a New Class of Compounds".
Ball, C.R., et al, *Chemical Pharmacology*, vol. 23, pp. 3173–3177, Pergamon Press, 1974, Printed in Great Britain, "Enzyme Activated Anti–Tumour Agents—Conjugates of p–Hydroxyaniline Mustard as Substrates for Hydrolytic Enzymes".
von Ardenne, M., et al, *Agressologie*, 17, 5 : 261–264 (1976) "Anti–cancer agents with activation in strongly hyperacidified tumor tissue: CMT Selectines".
Rubin, D., *Clinical Chemistry*, vol. 25, No. 10, pp. 1867–1868 (1979).
Baba, T., et al, *Gann*, 69, 283–284; Apr., 1978, "5–Fluorouracil L–β–D–Glucuronide as a Newly Synthesized Chemically Modified, Nontoxic Anticancer Drug".
Osinsky, S., et al, *Anticancer Research*, 7:199–202 (1987), "Tumour pH under Induced Hyperglycemia and Efficacy of Chemotherapy".
Eccles, S.A., et al, *Cancer Research*, 54, 5171–5177, Oct. 1, 1994, Regression of Established Breast Carcinomaj Xenografts with Antibody–directed Enzyme Prodrug Therapy against c–erbB2 p185.
Meyer, D.L., et al, *Cancer Research*, 53, 3956–3963, Sep. 1, 1993) "Site–specific Prodrug Activation by Antibody–β–Lactamase Conjugates: Regression and Long–Term Growth Inhibition of Human Colon Carcinoma Xenograft Models".
Henle, K.J., et al, *Radiation Research*, 115, 373–386 (1988), "Tumor–Targeted Cell Killing with 8–Hydroxyquinolyl–glucuronide".
*Nature*, vol. 252, Dec. 20/27, 1974, pp. 726–727 "Aplication of β–D–glucuronides and glucose together suggests a new direction for cancer chemotherapy".

(List continued on next page.)

Primary Examiner—Mukund J. Shah
Assistant Examiner—Deepak R. Rao
(74) Attorney, Agent, or Firm—Nixon & Vanderhye

(57) ABSTRACT

The present invention relates to compounds containing an anthracyclinone group such as doxorubicin, daunorubicin or a derivative thereof. The compounds of the invention also contain ester, glycoside or glucuronide structures which are hydrolyzed by the corresponding esterase, glycosidase or glucuronidase. These compounds possess potent cytotoxic activity which is developed after the hydrolysis of the ester or glycoside group of the compound and are effective in the inhibition of tumor cells and bacterial growth after activation.

44 Claims, 7 Drawing Sheets

OTHER PUBLICATIONS

Monson, T.P., et al, *Int. J. Radiation Oncology Biol. Phys.*, vol. 20,, No. 6, pp. 1263–1271, Jun. 1991, "Tumor–Targeted Delivery of 8–Hydroxyquinoline".

DiMaio, J.M., et al, *Surgery*, vol. 116, No. 2, pp. 205–213, Aug. 1994, "Directed enzyme pro–drug gene therapy for pancreatic cancer in vivo".

Bichko, V., et al, *Journal of Virology*, vol. 68, No. 8, P.5247–5252, Aug. 1994, "Introduction of Hepatitis Delta Virus into Animal Cell Lines via Cationic Liposomes".

Huber, B.E., et al, *Proc. Natl. Acad. Sci.*, vol. 91, pp. 8302–8306, Aug. 1994, "Metabolism of 5–fluorocytosine to 5–fluorouracil in human colorectal tumor cells transduced with the cytosine deaminase gene: Significant antitumor effects when only a small percentage of tumor cells express cytosine deaminasse".

Bosslet, K., et al, *Cancer Research*, 54:2151–2159, Apr. 15, 1994, "Tumor–selective Prodrug Activation by Fusion Protein–Mediated Catalysis".

Kimura, Ken–Ichi, et al, *The Journal Antibiotics*, vol. XLII, No. 1, pp. 127–131, Jan. 1989, "Structural Alteration of SN–07 Chromophore".

Cherif, A., et al, *Journal of Medicinal Chemistry*, vol. 35, No. 17, pp. 3208–3214 (1992), "N–(5, 5–Diacetoxypent–1–yl)doxorubicin: A New Intensely Potent Doxorubicin Analogue".

Cole, D.J., et al, *Cancer Immunol. Immunother.*, 38(5);299–303, May 1994—Abstract, "Histopathological analysis of metastatic melanoma deposits in patients receiving adoptive immunotherapy with tumor–infiltrating lymphocytes".

Pockaj, B.A., et al, *Cancer*, 15;73(6):1731–7, Mar. 1994—Abstract, "Localization of 111indium–labeled tumor infiltrating lymphocytes to tumor in patients receiving adoptive immunotherapy. Augmentation with cyclophosphamide and correlation with response".

Sweeney, M.J., et al, *Cancer Research*, 31, 477–478, Apr. 1971, "Possible In Situ Activation of Mycophenolic Acid by β–glucuronidate".

COMPOUNDS AND METHODS FOR THE SELECTIVE TREATMENT OF CANCER AND BACTERIAL INFECTIONS

FIELD OF THE INVENTION

The present invention relates to a new class of glucuronides, esters, and glycosides whose aglycone activity is more highly toxic than normally found for such compounds, as well as to methods of preparation of such glucuronides, esters, and glycosides. The present invention also relates to the treatment of tumors with an ester, or glucuronide and/or glycoside and optionally an enzyme such as an esterase, glucuronidase and/or glycosidase. The enzyme at the site of the tumor is either (i) a property of the tumor or (ii) is delivered there (targeted), or a combination of the two. The targeting is accomplished via a binding species or an organism. The invention further relates to the treatment of bacterial infections, in particular, infections having esterase, glucuronidase and/or glycosidase activity.

BACKGROUND OF THE INVENTION

The selectivity of anti-cancer drugs is poor and most of the drugs used for treatment have dose limiting toxicity (typically bone marrow toxicity but other tissues are affected depending on the anti-cancer drug). The use of doxorubicin, for example, is dose limited due to its cardiac toxicity and its myelosuppressive effect. Numerous attempts have been made to isolate related anthracycline drugs which show improved properties but doxorubicin and daunorubicin remain two of the most useful drugs for treatment of cancers and leukemias (Young, R C et al, New England J Medicine 1981, 305, 139–153; Zunino F and Capranico G, Anti-Cancer Drugs Design 1990, 5, 307–317; EP 0 441 218 A2).

The most interesting drugs for use as prodrugs are those which are toxic at low levels with IC50 (inhibitory concentration causing 50% inhibition of growth)<$10^{-5}$ M. Examples of such agents include morpholinyl anthracyclines (Streeter D G et al, Cancer Chemother Pharmacol 1985, 14, 160–164; U.S. Pat. No. 4,301,277), barminomycins (Uchida T, et al, The J of Antibiotics, 1988, XLI, 404–408) actinomycin D, and anthracycline analogs bearing latent alkylating substituents (U.S. Pat. No. 5,196,522). Morpholinyl anthracyclines such as compound 1 (see below) can dissociate in solution to form the reactive iminium compound 2; and compound 3, an anthracycline analog bearing a latent aldehyde, can undergo hydrolysis of the diacetoxy group by esterases in vivo followed by cyclization to form the analogous iminium compound 4.

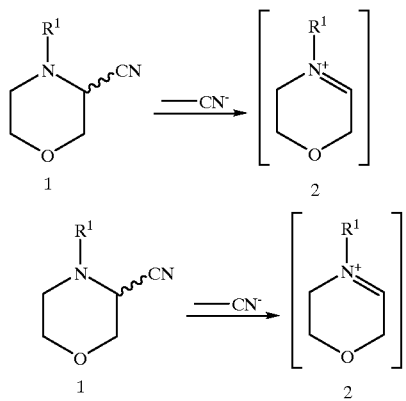

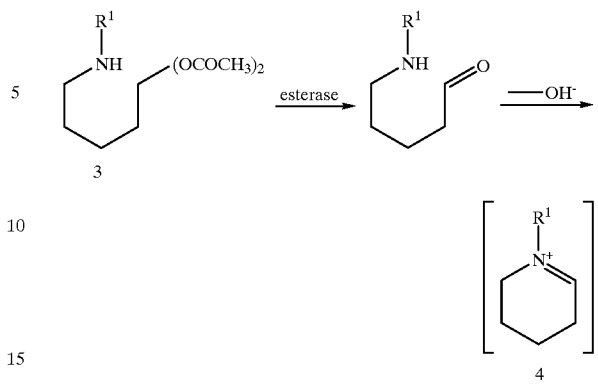

Reactive iminium ions are formed by the reaction of amines with carbonyl groups such as aldehydes and ketones.

The need for more toxic agents as prodrugs has been suggested by a number of workers in this area (Henle K J, et al Radiation Res, 1988, 115, 373–386). Attempts have also been made to improve the properties of the anthracycline cancer drugs by making glycoside modifications to generate activatable prodrugs (EP 0 441 218 A2, Leenders Ruben G G et al Tet Lett. 1995, 36, 1701–1704, EP 0 565 133 A2, WO 92/19639). These anthracycline glycosides do not make use of the more potent anthracyclines resulting in less desirable anthracycline prodrugs due to the clinical problems of large doses and increased cost of synthesis.

Antibodies which are specific for tumors are well known in the art. Tumor specific antibodies have been used to target toxins in attempts to develop cancer therapies.

The production of drug antibody conjugates has been achieved with some success in vitro but with disappointing results in tumor bearing mice and clinical studies (Garnett M C, et al Int J Cancer 1983, 31 661–670, Embleton M J et al Br J Cancer 1983, 47 43–49).

Attempts have been made to improve selective delivery of cytotoxic agents to tumors using antibodies coupled to enzymes. Conjugation of enzymes such as ricin and other ribosome inactivating proteins to antibodies has been used to target enzymes to tumors. In these studies, the enzyme is also the active toxin entering the cell and catalytically inactivating it by modification of the ribosomes (Moller G, Immunol Rev 1982;62).

In other studies, attempts have been made to use the activities of enzymes conjugated to targeting- antibodies to generate cytotoxic agents for targeted tumor killing. The early work on this principle used glucose oxidase as the enzyme (Philpott G D, et al J Immunology 1973, 111, 921–929). See also Parker et al, 1975 Proc Nat Acad Sci USA 72, 338–342.

WO 87/03205 discloses enzyme-coupled antibody, in which the enzyme is characterized by its ability to catalyze reactions which result in the death of cells bearing antigenic sites which the antibody can bind. See also U.S. Pat. No. 4,975,278. In animal studies, tumor regressions were seen with the targeting of the CC 49 anti tag 72 antibody as a conjugate to beta-lactamase to tumors followed by the treatment of the animals with a vinblastine prodrug substrate for beta-lactamase, Meyer et al (Cancer Res 1993 53, 3956–3963). In these studies, in addition to the antibody-enzyme conjugates, the drug antibody conjugates were evaluated and shown to be relatively ineffective and required very large doses of antibody when compared to enzyme activation.

Targeting of glycosidic enzymes has also been successfully used. In one example, a tumor specific antibody was chemically cross linked to the enzyme *E. coli* beta-glucuronidase and used to target a rat hepatoma cell line. This targeted beta-glucuronidase was used to activate p-di-2-chloroethylaminophenyl-beta-D-glucuronide prodrug to its active drug N,N-di-(2-chloroethyl) 4-hydroxyaniline. (Wang S M et al Cancer Res 1992 Aug. 15;52(16):4484–91).

In a further demonstration of this approach, a pan carcinoma antibody was chemically linked to *E. coli* beta-glucuronidase generating a conjugate which was able to specifically target various carcinoma cells. The prodrug used in this study was a glucuronide of epirubicin which resulted in a detoxification of the parent drug up to 1000 fold. This glucuronide was isolated from the urine of patients treated with epirubicin. The in vitro data demonstrated good levels of activation and cytotoxicity using these conjugates (Haisma H J et al Br J Cancer 1992 September;66(3):474–8).

In another study making use of (i) a conjugate of *E. coli* beta (galactosidase to an anti-CEA antibody Col1 and (ii) a galactoside of 5-fluorouridine, targeted activation was also demonstrated (Abraham R et al 1994 Cell Biophysics 24/25, 127–133).

Prodrug approaches have also been used clinically making use of the prokaryotic enzyme carboxypeptidase-G2 fused to anti CEA antibodies (Bagshawe K D et al Br J Cancer 1988 58:700–703). In a study aimed at producing a less immunogenic antibody fusion, which may have advantages over mouse antibodies and bacterial enzymes, a fusion with the human beta glucuronidase was made to a humanized anti CEA antibody. This was achieved by making a genetic construction allowing reproducible production of the therapeutic antibody (Bosslet K et al Br J Cancer 1992 65:234–238, EP 0501215 A2). This humanized anti CEA antibody human beta glucuronidase fusion protein has been demonstrated to activate a glucuronide of doxorubicin (see WO 92/19639) in tumor bearing mice to achieve some reduction in tumor growth and 10 fold higher levels of doxorubicin in the tumor (Bosslet K et al, 1994 Cancer Res. 54, 2151–2159). In an approach similar to that described by Bosslet et al., the use of human antibodies and human lysozyme has also been proposed to reduce the potential problems associated with immunogenic antibodies and enzymes (WO 90/07929).

The potential for the use of exogenous glycosidic enzymes in a non targeted format has been investigated (Tshiersch B, Schwabe K, Sydow G, and Graffi A Cancer Treat Rep 1977 61:1489–1493). In this study a combination of alpha-L-arabinofuranosidase from *Aspergillus niger* was used in combination with a prodrug form of beta-peltatin A, beta-peltatin A-alpha-L-arabinofuranoside. The aim of this approach was to make use of the lower pH optimum for the alpha-L-arabinofuranosidase to develop selective activation in tumors based on the lower pH found in tumors. This group also made use of the ability to affect the tumor pH by glucose infusion.

The potential for the use of endogenous glycosidic enzymes in a non targeted format has been investigated. U.S. Pat. Nos. 4,327,074; 4,337,760; 4,481,195; 4,584,368; and 5,005,588 describe the potential of using beta-glucuronidase activity present in tumors. The inventors note that the effect can be enhanced by the use of glucose and alkalinization to increase the differences in pH between the tumor and the normal tissues. The use of glucose allows the tumor pH to be lowered significantly and the use of a base such as sodium bicarbonate allows the urine pH and other areas of normal tissue to remain at pH in the range of 7.4. The lowering of the tumor pH can be as much as 0.5 pH unit in some cases (Cancer Res 49, 4373–4384, 1989). U.S. Pat. No. 4,248,999 discloses the use of 5-fluorouracil as a glucuronide (and other glycosides) by linking it to the C6 position of the uracil ring. Protocols for the improvement of therapy with glucuronide prodrugs have also been suggested which make use of the potential for endogenous glucuronidase activity, increasing the whole body pH and lowering the tumor pH.

The potential of using virus and/or nucleic acid targeted prodrug activation has also been investigated. In an example of this approach, the enzyme cytosine deaminase has been targeted using a retroviral vector to achieve the selective delivery and activation of the prodrug 5-fluorocytosine. This has been demonstrated with the generation of retroviral vectors which have incorporated the cytosine deaminase gene from yeast under control of the CEA promoter (Huber B E et al, 1993, Cancer Res 53, 4619–4626). In a similar approach the herpes simplex virus thymidine kinase (HSV-tk) has been incorporated into retroviral vectors to activate ganciclovir to its toxic phosphorylated form (J. Michael DiMaio et al 1994, Surgery 116, 205–213). Other viruses may be used in this targeting approach such as adenovirus, fowlpox, newcastles disease. These viruses are being explored in the treatment of cancer. The delivery of the virus may be direct through the use of an infectious particle which optionally has been engineered to have a selective tissue tropism (i.e., by inclusion of antibody binding domains (Chu et al, J Virol 1995, 69 2659–63)). In an alternative method the virus is targeted by the use of other vehicles such as liposomes in either a targeted (by binding moieties, i.e., antibodies) or untargeted fashion (Bichko V et al 1994, J Virology 68, 5247–5252). The targeting and delivery of genes to activate prodrugs can also occur via the delivery of DNA (not in the form of a virus). An encapsulation method can be used for delivery either via liposomes or through the use of viral like particles to package the DNA as has been demonstrated with a number of *E. coli* viruses.

SUMMARY OF THE INVENTION

The present invention relates to compounds containing an anthracyclinone group such as doxorubicin, daunorubicin or a derivative thereof. The compounds of the invention also contain ester, glycoside or glucuronide structures which are hydrolyzed by the corresponding esterase, glycosidase or glucuronidase. These compounds possess potent cytotoxic activity which is developed after the hydrolysis of the ester or glycoside group of the compound and are effective in the inhibition of tumor cells and bacterial growth, after activation. Included are compounds having the formula:

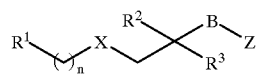

where:

$R^1$ is a radical of an anthracyclinone where the point of attachment is the $3^1$ nitrogen of the daunosamine sugar;

$R^2$ is H, alkyl having from 1 to 6 carbon atoms, phenyl or aromatic or heteroaromatic having, from 1 to 10 carbon atoms substituted with $NO_2$, CN, F, Cl, OH, OMe, or alkoxy having from 1 to 6 carbon atoms, COMe, $CF_3$, COOH, COO(alkyl or aryl) having from 1 to 10 carbon atoms;

$R^3$ is cyano, methoxy, ethoxy, alkoxy having from 3 to 18 carbon atoms, phenyloxy or aryloxy having from 1–10 carbon atoms substituted with $NO_2$, CN, F, Cl, OH, alkoxy having from 1 to 6 carbon atoms, COMe, $CF_3$, COOH, or COO (alkyl or aryl) having from 1 to 10 carbon atoms, acetoxy, propionyloxy, trimethylacetoxy, or benzoyloxy;

X=$CH_2$, O, S, or N substituted by H, alkyl or acyl having from 1 to 6 carbon atoms, phenyl, or aromatic or heteroaromatic having from 1 to 10 carbon atoms substituted with methyl, ethyl, acetyl or benzoyl;

n=2 if X=O, S, or substituted N;

n=1 or 2 if X=$CH_2$;

B is O, NHCOO, or one of the following substituted aromatics:

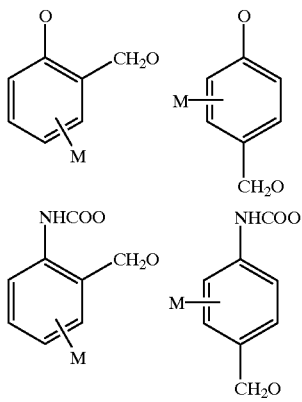

where M is H, $NO_2$, CN, F, Cl, OH, alkoxy having from 1 to 18 carbon atoms, COMe, $CF_3$, COOH, COO(alkyl or aryl) having from 1 to 10 carbon atoms, phenyl, aromatic or heteroaromatic having from 1 to 10 carbon atoms, methyl or alkyl having from 2 to 18 carbon atoms; and Z is a glycosyl, or substituted aliphatic or aromatic acyl having from 1 to 18 carbon atoms attached to the aromatic or carbamoyl O of B at the anomeric carbon of Z;

provided that where $R^3$ is aryloxy or acyloxy, BZ cannot be the same as $R^3$.

The invention, as well as other objects, features and advantages thereof, will be understood more clearly and fully from the following detailed description when read with reference to the accompanying Figures.

DETAILED DESCRIPTION OF THE INVENTION

The subject invention relates to a novel family of prodrugs for the treatment of cancer and bacterial infections which are based on the site specific activation of the prodrugs by various methods involving enzymes. Upon activation, the prodrugs are capable of undergoing spontaneous reactions leading to the formation of reactive iminium ions. In particular, the compounds of the present invention are activatable by glycosidases including glucuronidases, and esterases.

Advantageous anticancer drugs which can be modified according to the subject invention include anthracyclinones such as doxorubicin, deoxydoxorubicin and daunorubicin, epirubicin and idarubicin, or derivatives thereof.

Figure 5:
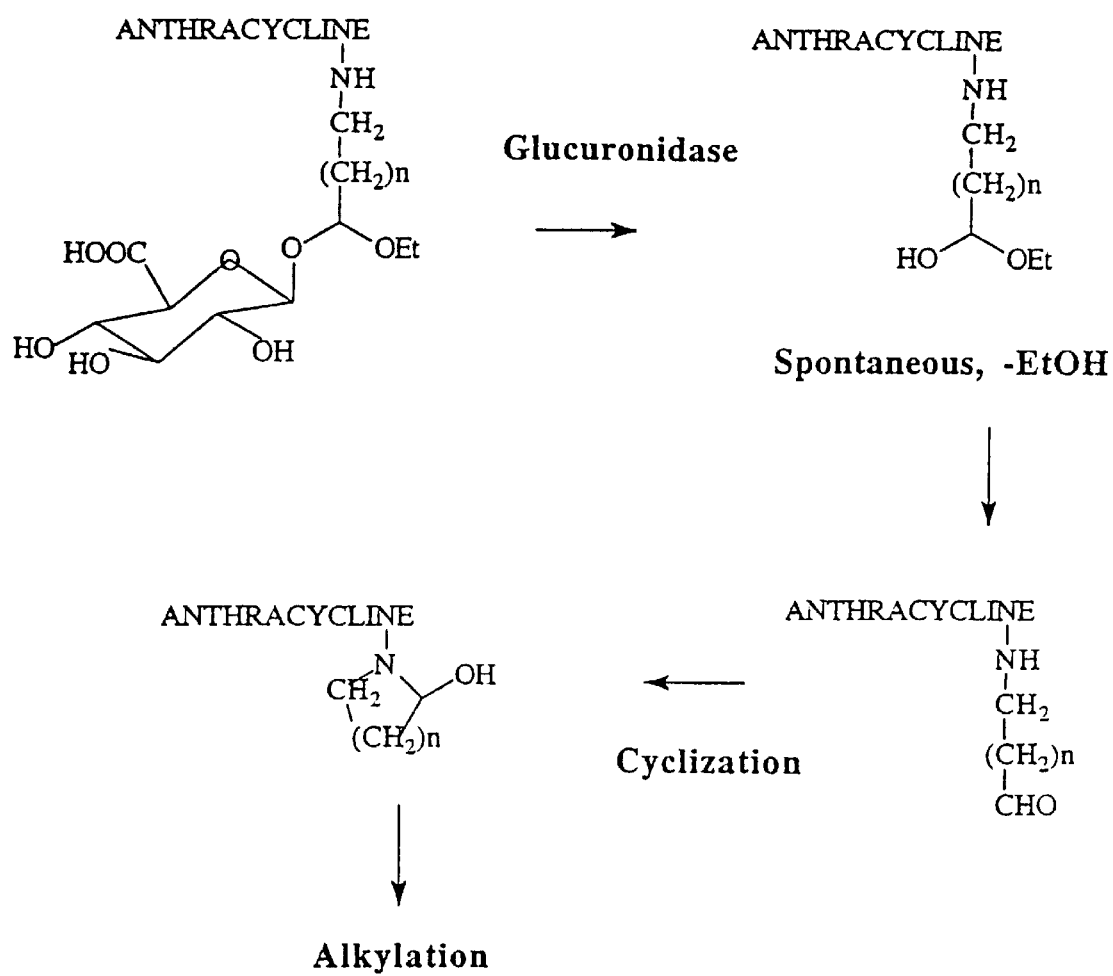
FIG. 5 schematically illustrates the potential mechanism of action of one example of the anthracylines class of prodrugs. This prodrug is structured to be activated by the enzyme glucuronidase.

The compounds of the invention are activated by enzymatic removal of glycoside structure to yield active intermediates, see FIG. 5. An example of activation using a glucuronide and glucuronidase is shown in FIG. 5.

The compounds of the invention are effective in the inhibition of human tumor growth and bacterial growth. The compounds may be divided into three classes based on the strategy of inactivation by glycosylation or esterification.

Figure 1:
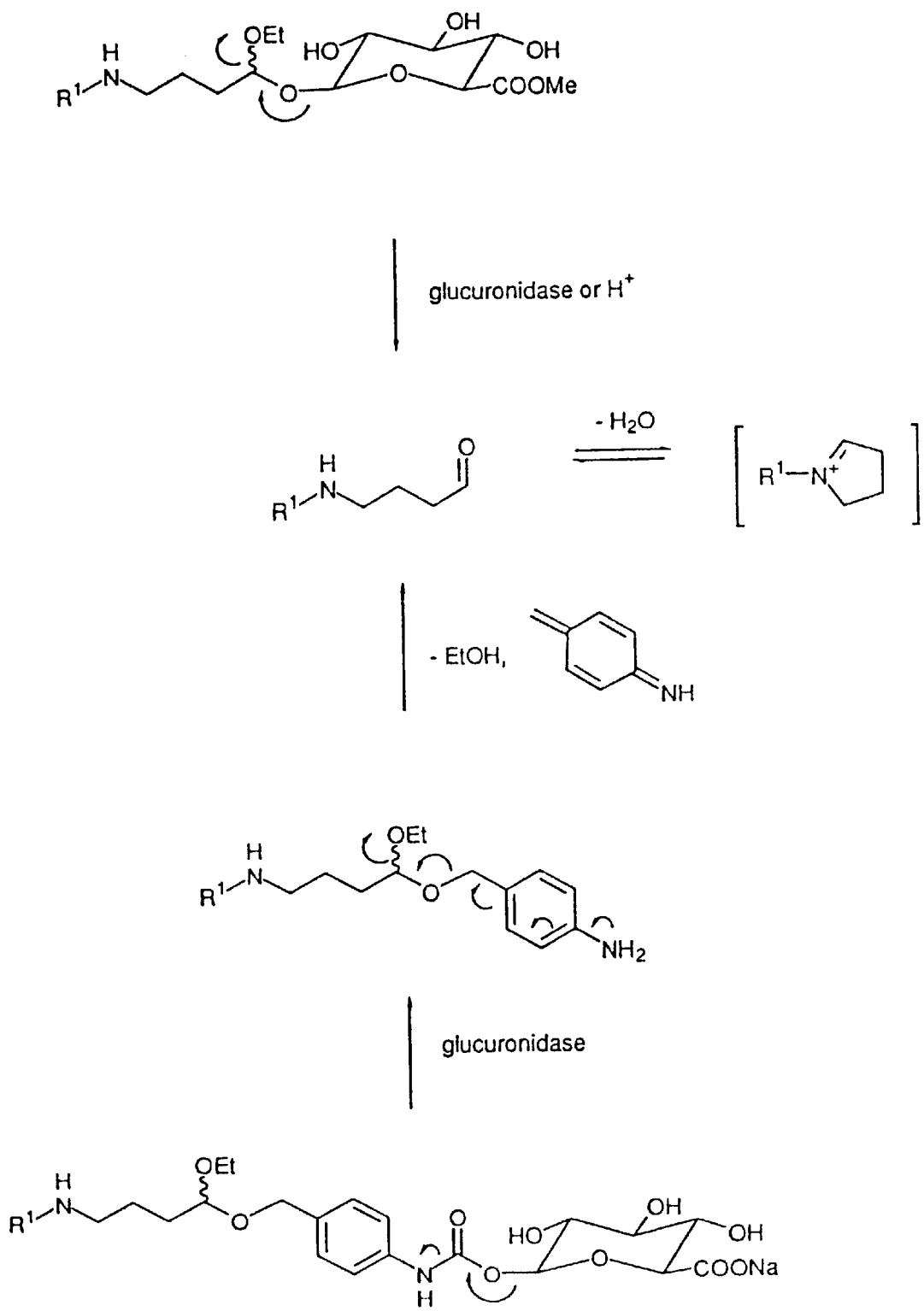
FIG. 1 illustrates the mechanisms by which two compounds of claim 1 can break down to form an amino aldehyde, which spontaneously forms the reactive iminium ion.
Figure 3:
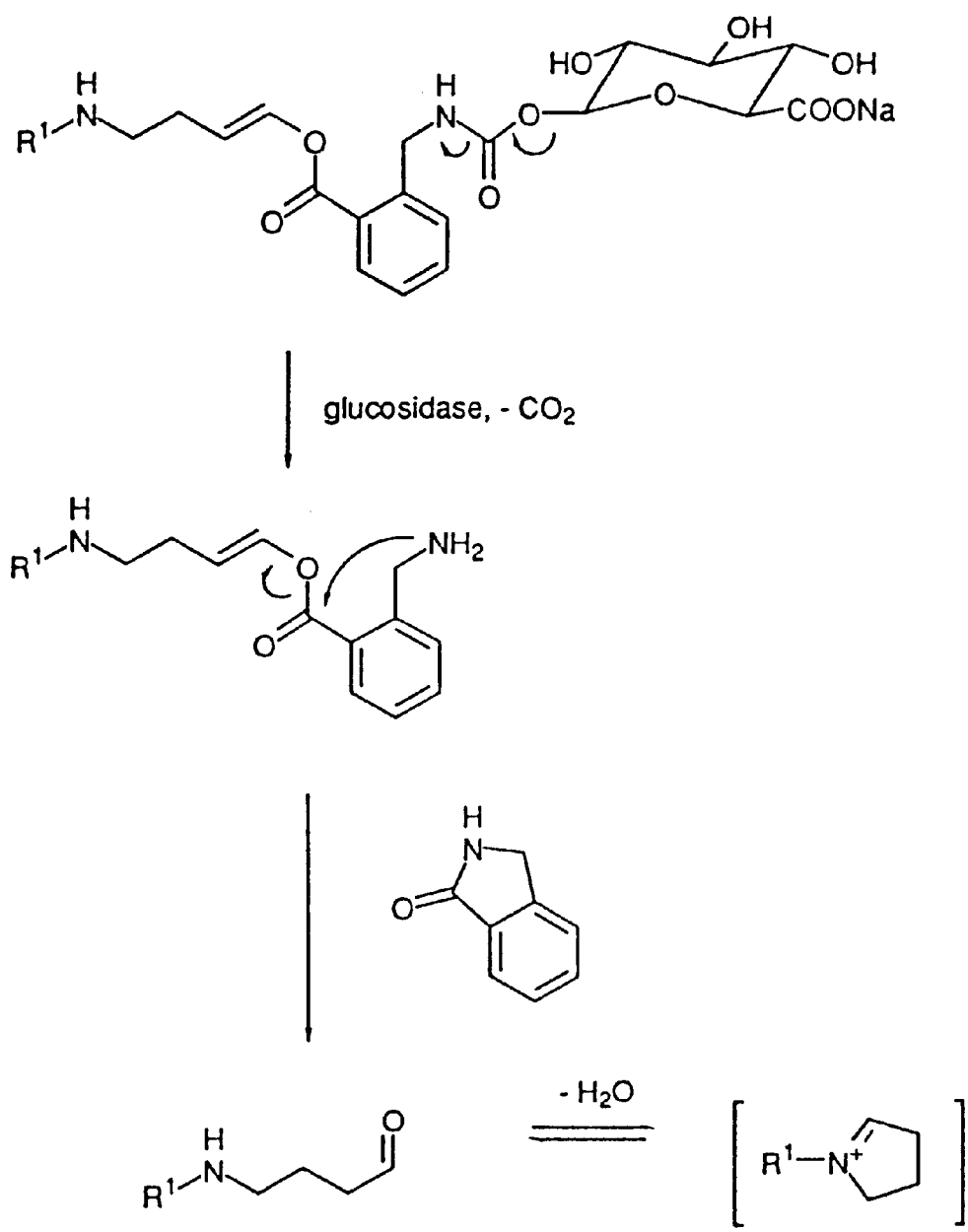
FIG. 3 illustrates another version of a self-immolative linker.

1. Glycosylation and esterification serves to mask a latent aldehyde or ketone from reaction with the amino group of the anthracycline. FIG. 1 illustrates the mechanisms by which two compounds of claim 1 can break down to form an amino aldehyde, which spontaneously forms the reactive iminium ion. The sugar can be directly attached to the latent aldehyde, or can be connected indirectly through a self-immolative linker. FIG. 3 illustrates another version of a self-immolative linker.

Figure 2:
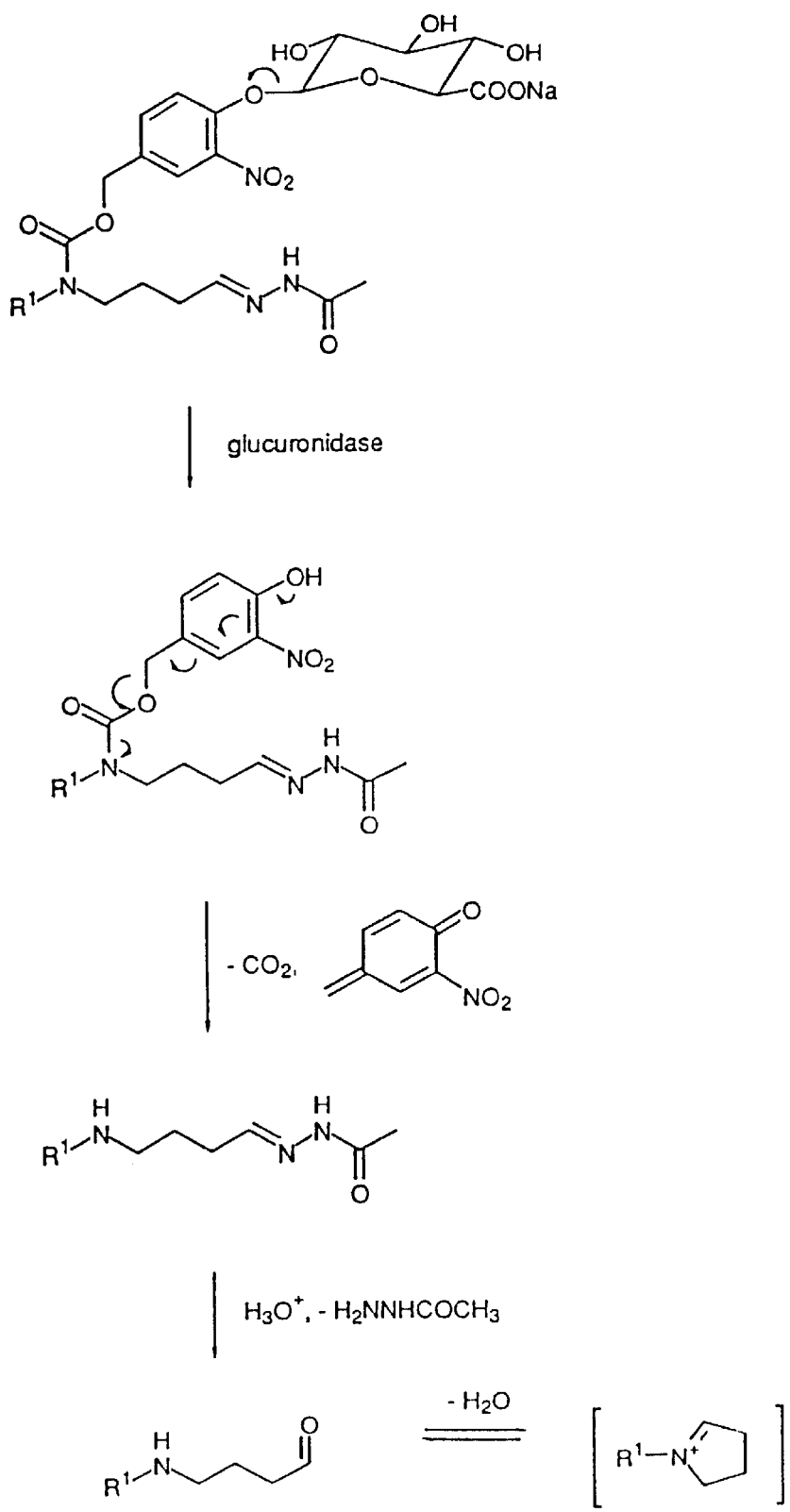
FIG. 2 illustrates the breakdown of an inactivated amino prodrug incorporating a self-immolative linker.

2. Glycosylation and esterification serves to mask the reactivity of the amino group of the anthracycline. The reactivity of the aldehyde or ketone is temporarily reduced as well, in order to inhibit undesirable intermolecular reactions with proteins, for example. FIG. 2 illustrates the breakdown of an inactivated amino prodrug incorporating a self-immolative linker. After the latent aldehyde is unmasked (hydrolysis at the acidic tumor pH), the amino aldehyde spontaneously forms the reactive iminium ion.

Figure 4:
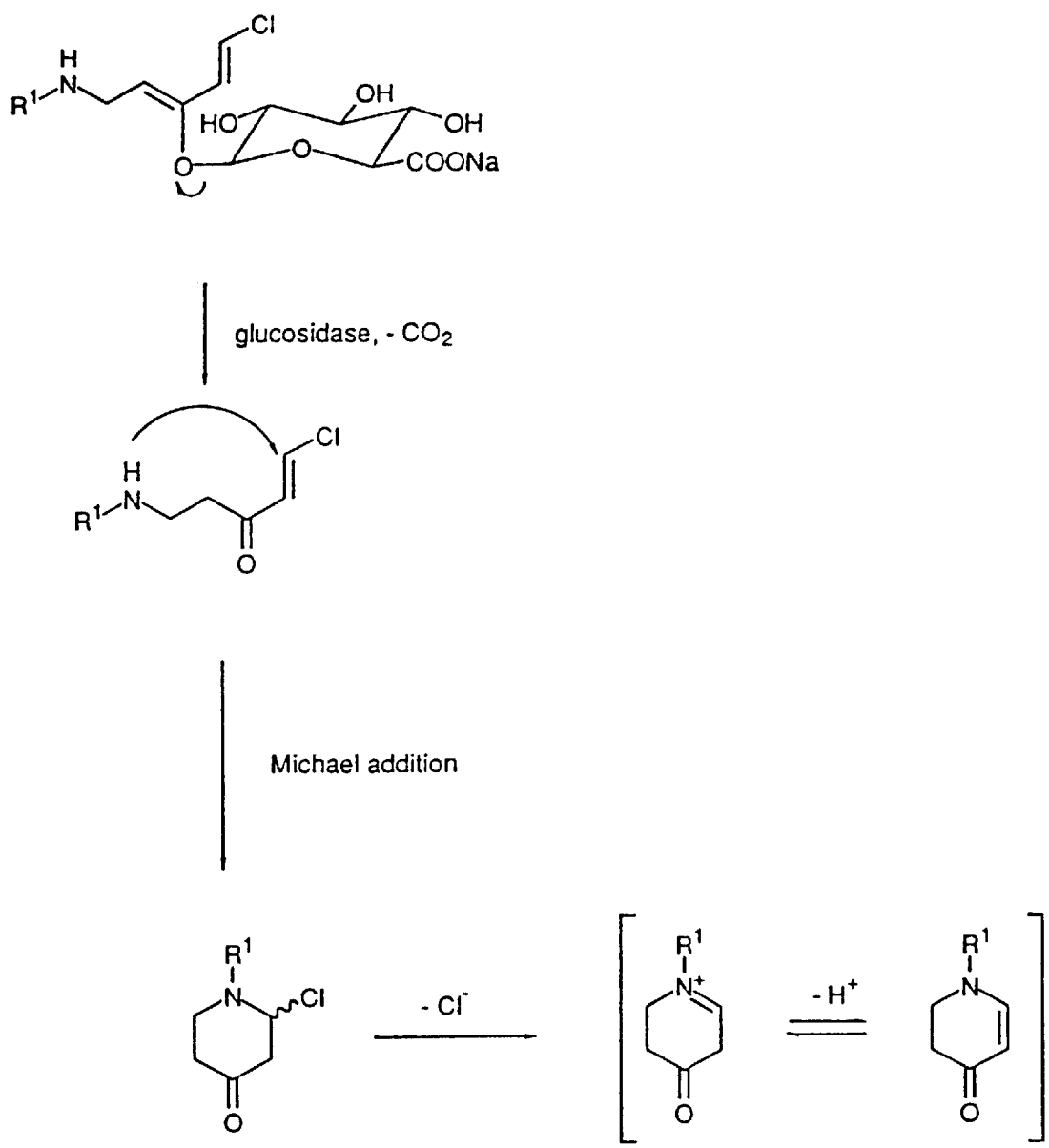
FIG. 4 illustrates breakdown of the prodrug to form an unsaturated ketone.

3. Glycosylation and esterification serves to mask a latent aldehyde or ketone which is reactive with the amino group of the anthracycline at the a or b position (as well as at the carbonyl) in a manner designed to give a reactive imminium ion. FIG. 4 illustrates breakdown of the prodrug to form an unsaturated ketone. Michael addition gives the a-halo amine, which dehalogenates spontaneously to form a reactive iminium ion.

I. Definitions

Organism means any bacteria, virus, parasite, or other living thing with a size less than 1 $\mu$M in any dimension.

Binding species means any molecule which has an affinity or avidity for another molecule greater than 1 mM. Examples of such molecules are usually defined as pairs where one binds to another of different or the same structure. Examples are: avidin/biotin; antibody/antigen; receptor/ligand; metal ion/ligand; protein/protein; lectin/carbohydrate; and nucleic acid/protein.

Humanized antibody means an antibody which has been modified to incorporate human sequences into it resulting in an antibody which is more like a human antibody. The term also includes antibodies which have been mutated to reduce immunogenicity.

Glycosyl group is a single molecular moiety added to another molecule. Examples of glycosyl groups which can be added to the molecules of the invention are galactosyl, glucuronyl, deoxy-glucosyl, iduronyl, glucosyl, N-acetyl glucosaminosyl, fructosyl, sialosyl, hyaluronosyl, sedoheptulosyl, xylulosyl, ribulosyl, ribosyl, xylitosyl, daunosaminosyl, arabinosyl, fucosyl, deoxy-ribosyl, mannosyl, N-acetyl-galactosyl, rhamnosyl, 3,6-anhydrogalactosyl, sialylfucosyl, and xylosyl. Molecules containing these glycosyl moieties are called glycosides. Molecules containing these glycosyl moieties, the glycosides, are substrates for the respective glycosidase.

Atithracyclinones are molecular moieties characterized by the presence of four fused six-membrered rings forming a substituted tetrahydronaphthacene quinone (aglycone) moiety conjugated via glycosidic linkages to a side chain containing one or more glycosyl groups. Most clinically important anthracyclines contain an amino glycosyl attached to the aglycone portion. The number and/or distribution of hydroxyls or methoxyls in the aglycone vary and semisynthetic anthracyclinones can contain functional groups not found in the natural products. Examples of compounds which form the anthracyclinones of the present invention are: adriamycin, daunomycin, carminomycin, rubidazone, carminomycin, zorubicin, epirubicin, idarubicin, deoxydoxorubicin, 4'-demethoxydaunorubicin, ditrisarubicins, betaclamycins, 2-hydroxyaclacinomycins, 4'-O-tetrahydropyranyladriamycin, barminomycins, baumycins, annamycin, pirarubicin, THP-doxorubicin, pirarubicin, aclarubicin, zorubicin, iododoxorubicin, AD-32, detorubicin, esorubicin, marcellomycin, quelamycin, rodorubicin, menogaril and nogalomycin. Examples are also presented in U.S. Pat. No. 4,411,834, hereby incorporated by reference.

Heteroaromatics are ring structures having from 5 to 8 atoms in the ring which contain in addition to carbon atoms, other atom types in the ring. These other atoms "heteroatoms" can be S, O, N, P, Si. In addition to these heteroatoms, the ring structure can also contain at least two double bonds as part of the ring structure. The number of heteroatoms in a ring can be from 1 to 4. Also, multiple rings can be fused to form a heteroaromatic as in the case of adenine. Examples of such heteroaromatics are furan, pyridine, indole, guanine, adenine, thiophene. These heteroaromatics can be derivatized with $NO_2$, CN, F, Cl, OH, alkoxy having from 1 to 6 carbon atoms, COMe, $CF_3$, COOH, or COO (alkyl or aryl) having from 1 to 10 carbon atoms, acetoxy, propionyloxy, trimethylacetoxy, or benzoyloxy, attached to the ring structure.

Glycosidase means a molecular species which is able to effect the removal of a glycoside or glucuronide from a molecular species containing a glycoside or glucuronide. Examples of glycosidases are glucuronidase, galactosidase, glucosidase, iduronidase, lysozyme, amylase, N-acetyl glucosaminidase, fructosidase, sialidase, hyaluronidase, etc., these being defined by the activity which each possess. Glycosidase activity is not a property solely of proteins. Synthetic chemistry can also generate similar activities (ability to hydrolyse the glycosidic bond). Examples of substrates for such glycosidases are lactose, glycogen, starch, cellulose, sucrose, nitrophenyl-maltohexoside, maltotriose, bromo-chloro-indolyl galactoside, methylumbelliferyl-N-acetylneuraminic acid, nitrophenyl glucoside.

A latent aldehyde or ketone is a functional group that can undergo conversion to form an aldehyde or ketone. For example, diacetoxy acetals such as $CH(OCOCMe_3)_2$ can undergo hydrolysis of the ester groups to form CH=O; the group $C=NNHCOCH_2CH_2SS(2-pyridyl)$ is very stable at pH 7.4, but has a half life of 1.8 hours at pH 5.0 and hydrolyzes to form C=O (*Biocojugate Chem.*, Vol. 2, 133–141, 1991); and the hydrolysis of silyl enol ethers such as $CH=CHOSiR_3$ to form $CH_2CH=O$ is well precedented in the literature.

II. Synthesis of the Compounds of the Invention

A. Synthesis of Glucuronyl Prodrugs of Anthracyclinone Drugs.

In general, synthesis is as follows: acetyl protected bromoglucuronic acid methyl esters are converted to the beta-benzyl glucuronates. At low temperature, the benzyl groups are cleaved to give the beta-alcohol anomer, which is quickly silylated to give the beta-trimethylsilyl glucuronide. Alternatively, acetyl protected, glucuronic acid esters with a free hydroxyl at the anomeric position are reacted with trimethylsilyldialkylamines to give the β-trimethylsilyl glucuronide with high selectivity. The silyl glycoside is reacted at low temperature with an alkenyl acetal to give the glucuronyl mixed acetal. Ozonolysis of the alkene produces an aldehyde, which is used for the reductive alkylation of the anthracyclines. The ester protecting groups are removed by saponification to give the prodrugs.

B. Synthesis of Diacyloxy Prodrugs of Anthracyclinone Drugs.

In general, synthesis is as follows: alkenyl alcohols are oxidized to the aldehydes using, an oxidant such as catalytic tetra-n-propylammonium perruthenate and N-methylmorpholine-N-oxide. The alkenyl aldehydes are reacted with carboxylic acid anhydrides using a Lewis acid activator such as boron trifluoride etherate to give the diacyloxy alkenes. Ozonolysis of the alkenes produces diacyloxy aldehydes, which are used for the reeductive alkylation of the anthracyclines.

III. Treatment of Cancer

Treatment of cancer in parients, i.e., mammals including humans, is achieved by administering the compounds and compositions of the invention. Examples of cancers which are treatable according to the invention are lung, colon, breast, pancreatic, ovarian, melanoma, and stomach cancers. Solid tumors offer the best opportunity for the use of the compounds of the present invention. These allow the generation of necrotic regions more readily able to activate the esters, glucuronides or glycosides of the present invention.

A. Activation of Prodrug by Endogenous Enzymes

In one embodiment of the invention, activation of the prodrug occurs due to endogenous enzyme in the tumor such as glucurionidase. Tumor pH is modulated using glucose and bicarbonate infusions which lower the tumor pH allowing the endogenous lysosomal enzymes to be more active than in normal tissue. The prodrug is then injected at doses from 1 miligram to 50 grams and at dosing intervals based on the response to the therapy and levels of prodrug products in the serum. The prodrug dose is advantageously in the range of 50 $\mu$g–5000 mg/m² with dose cycles of tumor pH modulation and prodrug administration each day for up to 20 days, depending on the level of non-specific activation as measured by the appearance of prodrug products in the serum. During the course of treatment patients are monitored for adverse cardiac toxicity, myelosuppression, liver and kidney function. This cycle of therapy is repeated a number of times (3–10 times) as required.

B. Glucuronide Therapy

In order to prepare the patient for glucuronide therapy, the tumor pH is lowered to improve the therapeutic effect of the glucuronidase activation. The patient is typically first given juices and asked to empty his bladder. This is followed by a dose of 100 g of glucose. After 30 min to 2 hrs, the patient then receives a drip which delivers 10% glucose and 60 milliequivalents of sodium bicarbonate. This drip delivers up to 1 liter over one hour. At 30 min into the drip, the patient empties his bladder to determine the effectiveness of the therapy in causing alkalanization of the urine. Alkalanization is also achieved by the use of inhibitors of carbonic anhydrase (i.e., acetazolamide) in combination with bicarbonate to achieve a more prolonged affect.

The treatment with the glucuronide drug is initiated when it has been determined that the glucose and bicarbonate drip has achieved alkanization of the urine. The analysis of the 30 min urine sample should show a pH above 7.4. The glucuronide prodrug is typically given as an infusion in order to maintain a sustained level of drug in the blood for a period of one hour or more. Alternatively, the prodrug is given as a bolus IV. The dose of the prodrug is a maximum of 500 mg/m2 per treatment round but can be fractionated into multiple doses. Patients may be eligible for further treatment based on the indications of toxic side effects. Treatment rounds occur at intervals of 3–6 weeks.

Patients are monitored for adequate organ function including hematological function (white cell count, platelet count), hepatic function (bilirubin, aspartate amino transferase, alanine aminotransferase), renal functions (creatinine levels) and pulmonary function (carbon monoxide diffusing capacity). This data is useful as a basis for controlling dose and intervals during treatment.

In one embodiment of the invention activation at a desired target is accomplished by causing the target to synthesize the activating species. For example, it is possible to direct tumor cells to synthesize enzymes which are able to activate prodrugs. For example, a retroviral vector which contains a glycosidic enzyme activity is generated which is capable of activating a compound of the invention. This viral vector is then targeted via the selective nature of the infectious agent for dividing cells or via the selective expression systems within the cell. Other viruses can be used in this targeting approach such as adenovirus, fowlpox, newcastles disease. The delivery of the virus can be direct through the use of an infectious particle which optionally has been engineered to have a selective tissue tropism (i.e., by inclusion of antibody binding domains (cf Winters)). In an alternative method, the virus is targeted by the use of other vehicles such as liposomes in either a targeted (by binding moieties, i.e., antibodies) or untargeted fashion (Bichko V et al 1994, J Virology 68, 5247–5252).

The targeting and delivery of genes to activate prodrugs can also occur via the delivery of DNA (not in the form of a virus). An encapsulation method is used for delivery either via liposomes or through the use of viral like particles to package the DNA, as has been demonstrated with a number of *E. coli* viruses. Thus, this type of system can be used to target the prodrug activation of the compounds of the invention. Targeting the expression is accomplished either via the targeting or the selective expression of glucuronidases or other glycosidases which then activate the prodrugs of the invention. This viral targeting of the activating agent gene to achieve the selective activation of the prodrugs of the invention can also be achieved using other organisms which show tropisms for tissues and organs. In an advantageous embodiment, the glucuronidase and/or glycosidase are expressed in these virally or organism based targeted systems in a form which does not diffuse away from the tumor or other target site, by making use of, for example, transmembrane domains of membrane binding proteins, the binding domains of antibodies, etc. known in the art.

Also the use of transformed cells may be used to target the delivery of enzyme activity to the site of therapy. See Cancer Immunol Immunother. 1994 Maj; 38(5): 299–303, Cancer, 1994, March 15; 73(6)1731–7.

C. Activation of Prodrug by Exogeneous Enzymes

In another embodiment, activation of the prodrug is accomplished by the administration of a dose of enzyme. Examples of glycosidase enzymes which are useful in the subject invention are glucuronidase, lysozyme, beta-galactosidase, alpha-galactosidase, beta-glucosidase, or other lysosomal enzymes which are able to hydrolyze glycosides. Ideally these enzymes should have a low pH optimum, i.e., below pH6. For example, from 1–100 mg of glucuronidase is administered followed by a clearance period during which the level of glucuronidase in the serum is monitored. At a time point after the injection of the enzyme, the level of enzyme reaches a level where the potential for activation of the prodrug is not significant. This time point will typically be from 12 hrs to 90 hrs after injection of the enzyme. At this time, when the level of enzyme has reached a level in serum not to cause over activation of the prodrug, the prodrug is injected at doses from 100 $\mu$g to 50 grams and at dosing intervals based on the patients response to the therapy, and/or levels of prodrug products in the serum. Advantageously, the prodrug dose is in the range of 50 $\mu$g–5000 mg/m$^2$ of prodrug with doses each day for up to 20 days depending on the level of non-specific activation (measured by the appearance of prodrug products in the serum).

Optionally, tumor pH is modulated using glucose and bicarbonate as described in the section above on activation by endogenous enzymes. This allows the tumor pH to be lowered permitting the accumulated glucuronidase to be more active than in normal tissues.

Adverse cardiac toxicity, myelosuppression, liver and kidney function are monitored during treament. This cycle of therapy is repeated a number of times (3–10 times) as required.

D). Activation of Prodrug by an Antibody-Enzyme Fusion

In the case of targeted glucuronidase and glycosidases, examples of targeting antibodies which can be used are OncoScint® (Cytogen Corp Princeton N.J.) which is capable of achieving in some cases tumor:normal tissue ratios of greater than 20:1 (Stern H, et al Cancer Investigation 1993, 11(2) 129–134), CA125, BR96, B72.3, CC49, Col1, 17-1A, and 16.88, which include both mouse, humanized and human antibodies (Siddiki B et al Int J Cancer 1993 54, 467–474; Weiner L M et al J Immunotherapy 13, 110–116; Muraro R, et al Cancer Res 1985 45, 5769–5780; Colcher D et al Cancer Res 1988 48, 4597–4603; Jager R D, et al Seminars in Nuclear Medicine 1993, XXIII, 165–179). See also U.S. patent application Ser. Nos. 07/773,042 and 07/919,851 each of which is hereby incorporated in its entirety by reference. These antibodies are linked by a chemical linkage or via the construction of genetic fusions. These molecules are dosed prior to the administration of compounds of the invention.

An antibody-enzyme fusion is administered at up to 1 $\mu$m in various dosing schedules, but typically in the range 1–200 mg per dose as a single dose which may be infused over a period of time from 10 min to 24 hr. The dose of antibody-enzyme can also be given in multiple dose injections. After antibody-enzyme infusion periodically the levels of enzyme are measured and the antibody titers. The typical time allowed for this clearance is from 1 to 14 days. When the levels of prodrug activating enzyme have reached a level at which little toxic activation can occur, the prodrug is administered. The prodrug is injected at doses up to 5 grams and at dosing intervals based on the response to therapy and levels of prodrug products in the serum. Advantageously, the prodrug dose is in the range of 50 µg–5000 mg/m of prodrug with doses each day for up to 20 days. The rate of administration will vary depending on the level of non-specific activation as measured by the appearance of prodrug products in the serum and monitoring of the dose limiting toxicity using HPLC analysis of extracted blood samples and serum chemistry analysis.

In addition, tumor pH modulation using glucose and bicarbonate to lower the pH within the tumor is optionally used in this embodiment. This increases the activity of the prodrug activating enzymes if these had pH optima which were lower than the normal leading to the delivery of more drug to the tumor.

During the course of treatment patients are monitored for adverse cardiac toxicity and myelosuppression. The cycle of therapy is repeated a number of times.

This targeting of the prodrug activating glycosidase activity is achieved using a number of binding species which have been shown to have selectivity for the tumors or tissues where selective activation is desired. Examples of targeting agents are growth factors, lectins, amino acids, vitamins for which there are receptors and/or transporters able to act as binding species for targeting. These targeting agents are linked to the glycosidase activity to allow selective accumulation of the activating enzyme mediated via these binding species.

IV. Use of Glycoside Prodrugs as Antibiotics

The glycoside prodrugs of the invention are useful in the treatment of bacterial infections where the bacteria involved have a specific glycosidase activity. Examples of such bacteria are streptococci, staphylococci, and *E. coli*. Treatment is similar to that described above for cancer but there is no need for hyperacidification. The alkalinization of the urine is carried out to reduce the non-specific activation in the bladder as described above. Bicarbonate drips or drug treatments (e.g., acetazolamide) can be used. Having established this alkalinization, the prodrug is given via the bicarbonate drip or by intravenous injection in a suitable vehicle. Alkalinization can also be achieved by oral bicarbonate.

In one embodiment of the invention, the prodrugs are used without alkalization due to the stability of the glycoside pro-group to the conditions present in the bladder.

V. Formulation and Administration

The present invention also encompasses pharmaceutical compositions, combinations and methods for treating cancers and other tumors. More particularly, the invention includes combinations comprising immunoconjugates (targeting protein and catalytic protein, or targeting antibody and catalytic antibody (bispecific antibodies)) and the corresponding prodrug or prodrugs for use in a method for treating tumors wherein a mammalian host is treated in a pharmaceutically acceptable manner with a pharmaceutically effective amount of a targeting protein catalytic protein conjugate or conjugates or bispecific antibody or antibodies and a pharmaceutically effective amount of a prodrug or prodrugs. In addition the invention includes combinations comprising immunoconjugates (targeting protein and catalytic protein, or targeting antibody and catalytic antibody (bispecific antibodies)) and the corresponding prodrug or prodrugs for use in a method for treating tumors wherein a mammalian host is treated in a pharmaceutically acceptable manner with a pharmaceutically effective amount of a targeting protein catalytic protein conjugate or conjugates or bispecific antibody or antibodies and a pharmaceutically effective amount of a prodrug or prodrugs. The combination and methods of this invention are useful in treating humans and animals.

The prodrugs and/or the binding species or organism is administered by any suitable route, preferably parenterally, e.g., by injection or infusion. These compounds are administered using conventional modes of administration including, but not limited to, intravenous, intraperitioneal, oral, intralymphatic, or administration directly into the tumor. Intravenous administration is particularly advantageous.

The compositions of the invention—comprising the binding species or organism or prodrugs—can be in a variety of dosage forms which include, but are not limited to, liquid solutions or suspensions, tablets, pills, powders, suppositories, polymeric microcapsules or microvesicles, liposomes, and injectable or infusible solutions. The preferred form depends upon the mode of administration and the therapeutic application. For example, oral administration of the antibody-enzyme conjugate or bispecific antibody may be disfavored because the conjugate proteins tend to be degraded in the stomach if taken orally, e.g., in tablet form.

Suitable formulations of the binding species or organisms or prodrug for parenteral administration include suspensions, solutions or emulsions of each component in oily or aqueous vehicles and optionally contain formulatory agents such as suspending, establishing and/or dispersing agents. Alternatively, the binding species or organism or prodrug is in powder form for reconstituting with a suitable vehicle, e.g., sterile pyrogen-free water before use. If desired, the immunoconjugate antibody and/or prodrug is presented in unit dosage form. Formulations are conveniently prepared in isotonic saline for injection.

The most effective mode of administration and dosage regimen for the compositions of this invention depends upon the severity and course of the disease, the patient's health and response to treatment and the judgement of the treating physician. Accordingly, the dosages of the binding species, organisms and prodrugs should be titrated to the individual patient.

Nevertheless, an effective dose of the binding species or organisms of this invention is in the range of from about 1.0 to about 100 mg/m$^2$. An effective dose of the prodrug of the invention will range from 100 µg–100 g/m$^2$. the precise doses at which the immunoconjugate and prodrug will be administered will depend on the route of administration, body weight, and pathology of the patient, the nature of the prodrug, and the catalytic properties of the immunoconjugate. Since the prodrug is less cytotoxic than the parent drug, dosages in excess of those recognized in the art for the parent drug may be used.

EXAMPLES

Example 1

Synthesis of Methyl 2,3,4-Tri-O-acetyl-1-O-trimethylsilyl-β-D-glucuronate 3

Figure 7:
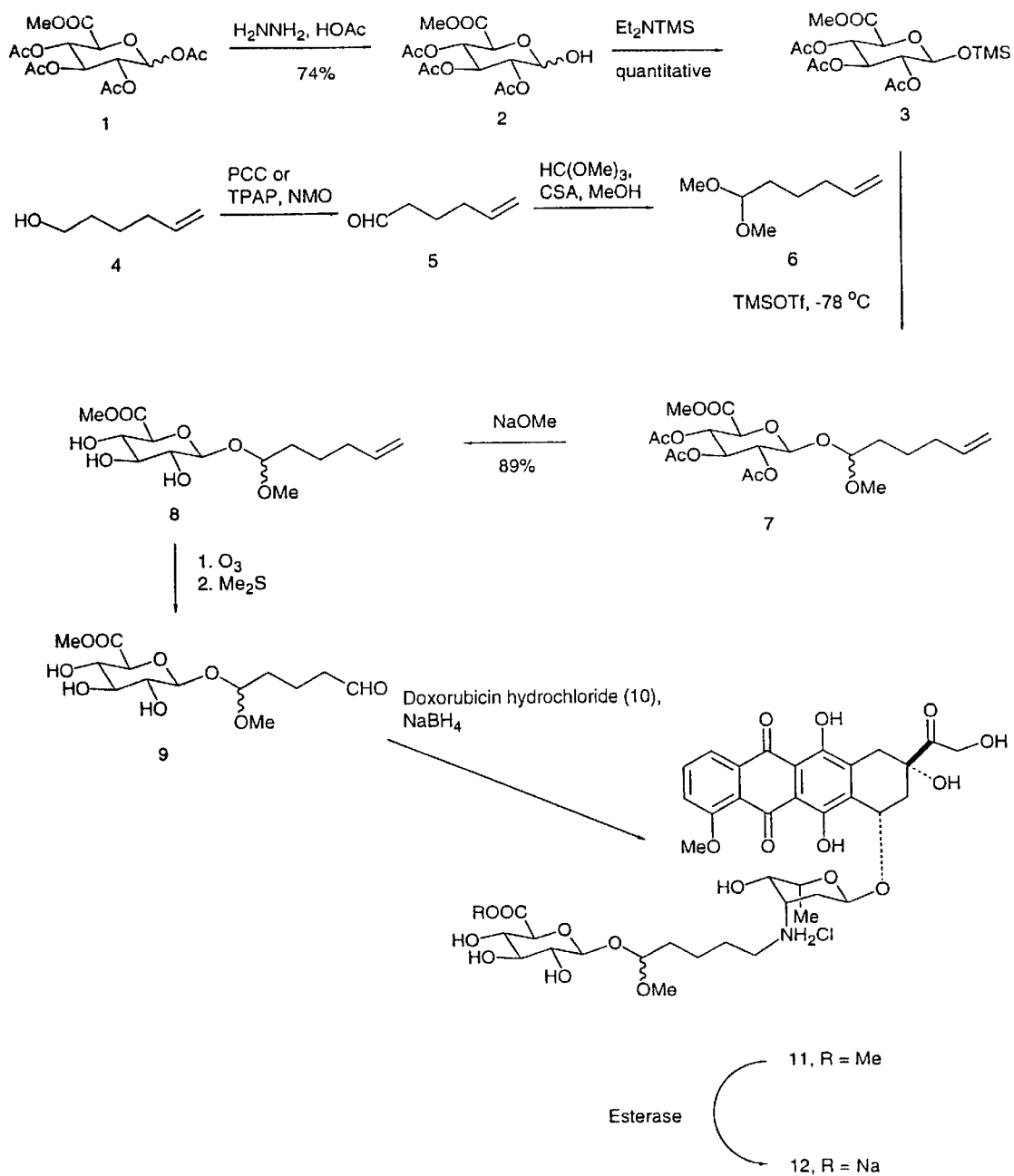
FIG. 7 is a schematic illustration of a synthetic route to a glucuronide of doxorubicin (Example 3).

The compounds referred to in this synthesis are shown in FIG. 7. The numbered intermediates of the Figure are cross-referenced in the text below in bold.

Methyl 2,3,4-tri-O-acetyl-1-O-trimethylsilyl-β-D-glucuronate 3 can be prepared following a published three-reaction procedure (see compounds 1–4 in FIG. 2; L. F. Tietze, et al., *Carbohydrate Res.*, Vol. 148 (1986), 349–352); however, this procedure is technically demanding because it requires careful control of temperature. A simpler and more direct synthesis (compounds 1–3 in FIG. 7) has been developed: the commercially available tetraacetate 1 was converted to a mixture of the α and β pyranoses 2 using a mixture of hydrazine and acetic acid in DMF. The anomeric mixture was treated with N-trimethylsilyldiethylamine in acetone at room temperature to give the desired β-silyl glucuronide 3 highly selectively (β/α>98:2 by NMR).

The stereoselectivity of this reaction can be attributed to three factors: 1. Under the reaction conditions, the α and β pyranoses undergo facile anomerization. 2. Despite the fact that the α anomer is favored thermodynamically, the β-alkoxy anion is more reactive kinetically (Schmidt, et al., *Tetrahedroti Leit.*, Vol. 25 (1984), 821; *Liebigs Ann. Chem.*, (1984), 1343). 3. Unfavorable 1,3-diaxial interactions with the glucuronyl H3 and H5 disfavor reaction between the bulky silylating reagent and the a alkoxide.

In detail, the synthesis is as follows:

Methyl 2,3, 4-tri-O-acetyl-D-glucuronate 2

Methyl 1,2,3,4-tetra-O-acetyl-D-glucuronate 1 (2.50 g, 6.7 mmol) was added in one portion to a solution of hydrazine hydrate (380 mL, 8.0 mmol) and acetic acid (460 mL, 8.0 mmol) in 20 mL of DMF at room temperature. After 1 h, the mixture was partitioned between ethyl acetate (3×100 mL) and water (100 mL), 5% $KHCO_3$ (100 mL), and 0.1 M HCl (100 mL), and the organic phases were washed with brine (50 mL), dried over anhydrous $MgSO_4$ and concentrated in vacuo. The residue was purified by flash chromatography (40, 50, and 60% ethyl acetate/hexane) to give 0.21 g of recovered starting material (8%) and 1.66 g of the product as a colorless foam (74%), a 3.6:1 mixture of α and β anomers by NMR. Crystallization from ether/hexane gave the pure α anomer. $R_f$ 0.26 (50% ethyl acetate/hexane); mp 104.5–109.5 ° C.; $^1H$ NMMR ($CDCl_3$) δ 2.01 (s, 3), 2.02 (s, 3), 2.06 (s, 3), 3.72 (s, 3), 4.56 (d, 1, J=10.1, H5), 4.87 (dd, 1, J=3.6, 10.2, H2), 5.11–5.18 (m, 1, H4), 5.51 (d, 1, J=3.6, H1), 5.52–5.58 (m, 1, H3); $^{13}C$ NMR ($CDCl_3$) δ 20.47, 20.60, 52.88, 67.89, 69.06, 69.45, 70.70, 90.14, 168.50, 169.68, 170.04, 170.17.

Methyl 2,3,4-tri-O-acetyl-1-O-trimethylsilyl-δ-D-glucuronate 3

Four mL of N-trimethylsilyldiethylamine was added to a solution of glucuronate 2 (700 mg, 2.0 mmol) in 4 mL of acetone. After 40 h at room temperature, the volatile components were evaporated in vacuo. The resultant brown solid, greater than 98% the b-silyl glucuronide 3 by NMR, was sufficiently pure to be used without further purification. The residue can be crystallized from ether and hexane. $^1H$ NMR ($CDCl_3$) δ 0.15 (s, 9), 2.01 (s, 6), 2.03 (s, 3), 3.74 (s, 3), 4.00–4.07 (m, 1, H5), 4.79 (d, 1, J=7.4, H1), 4.90–4.95 (m, 1), 5.18–5.26 (m, 2); $^{13}C$ NMR($CDCl_3$) δ −0.06, 20.47, 20.60, 52.76, 69.44, 72.06, 72.66, 73.11, 95.56, 167.15, 169.17, 169.30, 170.14.

Example 2

Synthesis of Glucuronide Prodrugs of the Invention

Figure 6:
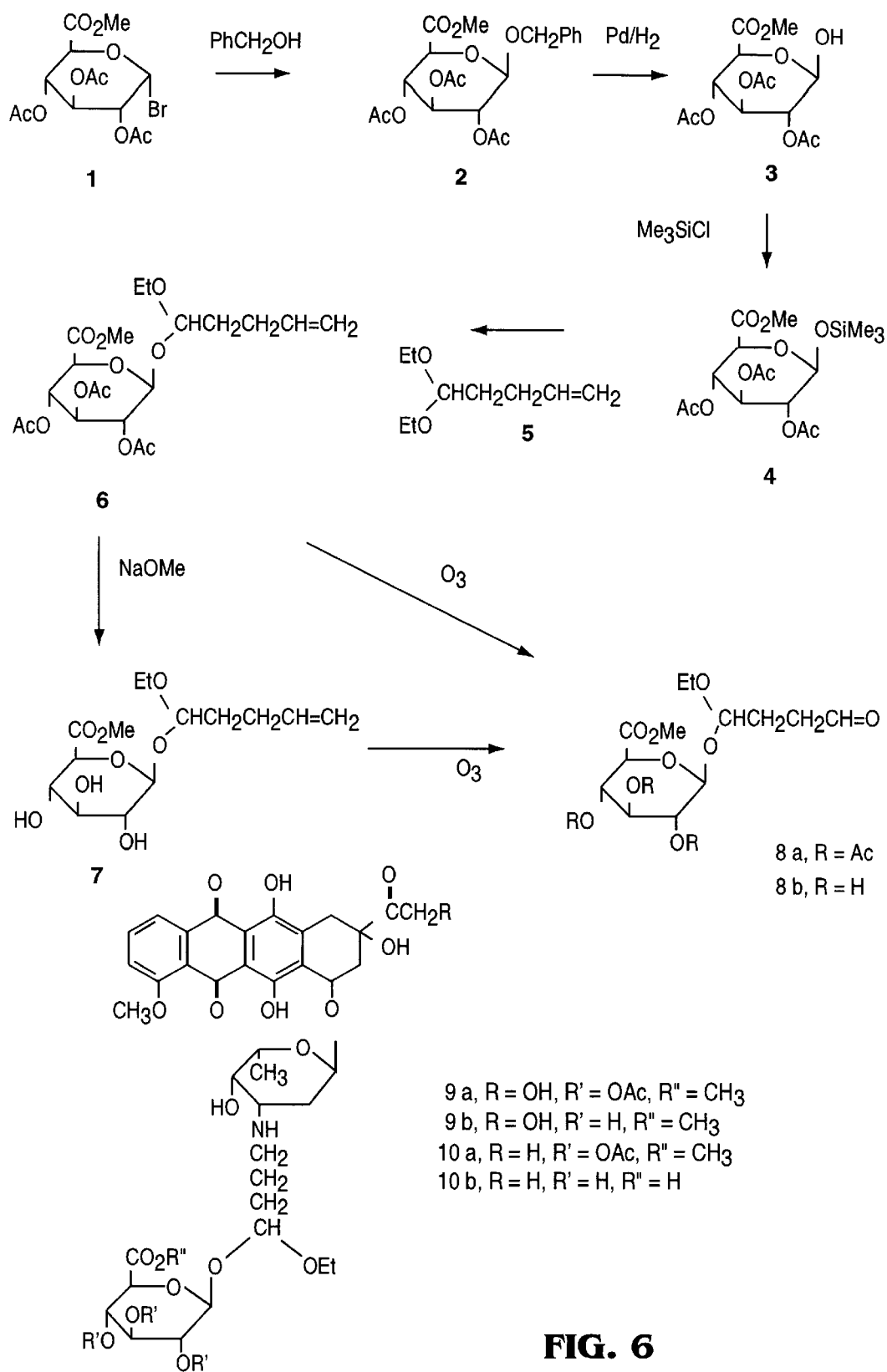
FIG. 6 is a schematic illustration of a synthetic route to a glucuronide of doxorubicin and daunorubicin (Example 2).

The compounds referred to in this synthesis are shown in FIG. 6. The numbered intermediates of the Figure are cross-referenced in the text below in bold.

Compounds 9b and 10b are glucuronide prodrugs of doxorubicin and daunorubicin, respectively. Compound 9b will undergo esterase hydrolysis of the methyl ester in vivo before glucuronidase catalyzed removal of the glucuronic acid to give the drug. Compound 10b will undergo glucuronidase catalyzed removal of the glucuronic acid to give the drug without prior transformation.

Compounds 9b and 10b were made starting from methyl 2,3,4-tri-O-acetyl-1-O-trimethylsilyl-β-D-glucuronate 4 (see Example 1 for its preparation). Compound 4 was reacted with the readily available compound 5 using a Lewis acid catalyst at low temperature following the method described by Tietze, et al. (*Carhohydrate Res.*, Vol. 180 (1988), 253–262). Working carefully, the β-glucuronide 6 can be obtained selectively, but acid catalyzed equilibration of compound 4 to the more stable α anomer prior to coupling, which will give the α-glucuronide, can be problematic. Compound 6 was reacted with ozone to give compound 8a. Alternatively, the acetate protecting groups of compound 6 were removed by methanolysis to give compound 7, which was reacted with ozone to give aldehyde 8b. Compound 8b underwent reductive amination with doxorubicin to give the prodrug 9b. Compound 8a underwent reductive amination with daunorubicin to give compound 10a, and the ester groups of compound 10a were saponified to give prodrug 10b.

In detail, the synthesis is as follows:

4-Pentenal dielhyl acetal 5

Boron trifluoride diethyl etherate (0.2 mL) was added, with stirring, to a solution of 4-pentenal (Cherif, A.; Farquhar, D. N-(5,5-diacetoxypent-1-yl)doxorubicin: A new intensely potent doxorubicin analogue. J. Med. Chem. 35, 3208–3214 (1992)) (2.5 g, 29.8 mmol) in ethanol (150 mL). The mixture was refluxed for 10 min under nitrogen, then the ethanol was removed under reduced pressure. The residue was taken up in dichloromethane (25 mL), and the solution was washed with 10% sodium acetate solution (15 mL) and water (2×10 mL). The organic layers were combined, dried over anhydrous sodium sulfate, and evaporated. The residue was chromatographed on a column of silica gel using chloroform/methanol (97:3) as eluent. 4-Pentenal diethyl acetal was obtained as an oil (4.5 g, 96%). $^1H$ NMR ($CDCl_3$) δ 5.88–5.61 (m, 1 H, H4), 5.03–4.87 (m, 2 H, H5), 4.38 (t, 1 H, J=7, H1), 3.30–3.61(m, 4 H, 2×$CH_2$), 2.07–1.96 (m, 2 H, H2), 1.64–1.53 (m, 2 H, H3), 1.09 (t, 6 H, J=7, 2×$CH_3$).

Methyl 1-O-[(1"RS)-1'-ethoxypent-4"-enyl]-2,3,4-tri-O-acetyl-β-D-glucopyranuronate 6

Trimethylsilyl trifluoromethanesulfonate (0.2 mL of a 0.1 M solution in chloroform; 0.02 mmol) was added, with stirring, to a solution of 5 (100 mg, 0.63 mmol) and methyl 2,3,4-tri-O-acetyl-1-O-trimethylsilyl-δ-D-glucopyranuronate 4 (L. F. Tietze and R. Seele, Stereoselective synthesis of 1-O-trimethylsilyl α- and β-D-glucopyranuronate. Carbohydrate Res. 148, 349–352 (1986)) (90.5 mg, 0.22 mmol) in dry dichloromethane (3 mL) at −70 ° C. under a dry nitrogen atmosphere. The mixture was kept at −70 ° C. for 2 days, then triethylamine (0.1 mL) was added to quench the reaction. The solvent was evaporated, and the residue was taken up in chloroform (10 mL) and washed with saturated sodium bicarbonate (10 mL) and sodium chloride (10 mL). The organic extract was dried ($MgSO_4$) and evaporated, and the residual solid was chromatographed on a column of silica (25 cm×2 cm ) using a stepwise gradient of hexane-ethyl acetate (10:0, 20 mL; 7:3, 100 mL; 6:4, 100 mL; 5:5, 150 mL). The eluted fractions were monitored by TLC using iodine vapor to visualize the products. The title compound was obtained as a solid. $^1H$ NMR ($CDCl_3$) ⊕ 5.63–5.86 (m, 1 H, H4"), 5.24–5.18 (m, 2

H, H3,4), 5.05–4.99 (m, 1 H, H2), 4.96–4.89 (m, 2 H, H5"), 4.83–4.74 (m, 1.5 H, H1 (S), H1 (R), H1" (S)), 4.65 (t, 0.5 H, J=6.0, H1" (R)), 4.02–3.97 (m, 1 H, H5), 3.71 (s, 3 H, $CO_2Me$), 3.68–3.43 (m, 2 H, $CH_2$), 1.99, 1.98, 1.96 (3 s, 9 H, 3 Ac), 1.74–1.67 (m, 2 H, H3"), 2.09–2.01 (m, 2 H, H2"), 1.15 (t, 3 H, J=7, $CH_3$); MS (FAB) m/z 447 (M +H)+.

Methyl 1-O-[(1"RS)-1'-ethoxypent-4"-enyl]-β-D-glucopyranuronate 7

Compound 6 (72 mg, 0.167 mmol) was dissolved in dry methanol (2 mL), and 0.4 mL of a solution of sodium methoxide (42 mg, 0.78 mmol) in methanol (10 ml) was added. The reaction mixture was maintained at ambient temperature for 3 h, then evaporated under reduced pressure. The residue was purified on a thick layer of silica to give the title compound, 7, as a white solid. $^1$H NMR δ 5.88–5.74 (m, 1 H, H4"), 5.07–4.90 (m, 2 H, H5"), 4.81 (t, 0.5 H, J=6.0, H1, (S)), 4.70 (t, 0.5 H, J=6.0, H1, (R)), 4.60 (d, 0.5 H, J=7.5, H1", (S)), 4.53 (d, 0.5 H, J=7.5, H1", (R)), 3.84 (s, 3 H, $CO_2Me$), 3.91–3.47 (m, 6 H, H2, H3, H4, H5, O$CH_2CH_3$), 2.13–2.05 (m, 2 H, H2"), 1.79–1.70 (m, 2 H, H3"), 1.19 (t, 3 H, $CH_3$).

Methyl 1-O-[(1"RS)-1"-ethoxy]-4"-oxobutyl-2, 3, 4-tri-O-acetyl-β-D-g glucopyranuronate 8a A solution of compound 6 (79.6 mg, 0.185 mmol) in dichloromethane (5 mL) was placed in a cylindrical gas absorption vessel with an inlet dispersion tube extending to the base. The vessel was cooled to −70 °C. in a dry ice/acetone mixture, and ozone was introduced. Ozonization was continued until the reaction was complete (until the mixture turned blue as a result of formation of the ozonide, approximately 20 min). Dimethyl sulfide (54 μL, 0.74 mmol, 4 equiv) was added, and the mixture was stirred overnight to reduce the ozonide to the corresponding aldehyde. The excess dimethyl sulfide was evaporated, and the residue was chromatographed on a column of silica (23 cm×2 cm) using a stepwise gradient of hexane-ethyl acetate (10:0, 50 mL; 7:3, 150 mL; 6:4, 100 mL). 100 fractions of approx. 3 mL each were collected. The major product (fractions 62–67) was identified by NMR as the title compound. $^1$H NMR (CDCl$_3$) δ 9.72 (s, 1 H, CHO), 5.25–5.18 (m, 2 H, H3,4), 5.09–5.01 (m, 1 H, H2), 4.85–4.75 (m, 2 H, H1 (R,S), H1 "(R,S)), 4.02–3.97 (m, 1 H, H5), 3.73 (s, 3 H, $CO_2Me$), 3.65–3.39 (m, 2 H, $CH_2$), 2.57–2.51 (m, 2 H, H3"), 1.98–1.92 (m, 2 H, H2"), 2.03, 2.02, 2.00 (3 s, 9 H, 3 Ac), 1.16 (t, 3 H, J=7, $CH_3$).

Methyl 1-O-[(1"RS)-1"-ethoxy-4"-oxobutyl]-β-D-glucopyranuronate 8b

A solution of compound 7 (56.3 mg, 0.185 mmol) in dichloromethane (15 mL) was ozonized for 20 minutes, as described for 8a. The intermediate ozonide was reduced with dimethyl sulfide (54 μ, 0.74 mmol, 4 equiv). The product was purified by preparative chromatograpy on silica.

N-[(4"RS)-4"-Ethoxy-4"-(methyl 2"'", 3"'", 4"'"-tri-O-acetyl-β-D-glucopyranuronyloxy)buty]doxorubicin hydrochloride 9a A solution of sodium cyanoborohydride (1 M in tetrahydrofuran; 11.3 μL, 0.0113 mmol) was added to a stirred solution of doxorubicin hydrochloride (10 mg, 0.017 mmol) and compound 8a (15 mg, 0.035 mmol) in acetonitrile-water (2:1) (5 mL). The mixture was stirred under a nitrogen atmosphere at room temperature in the dark for 1 h. When reaction was complete (as evidenced by TLC of a 5 μL aliquot), the solution was diluted with water (8 mL), and extracted repeatedly (10×10 mL) with chloroform-methanol (5:1). The combined extracts were dried and evaporated to give a red amorphous solid which was purified by preparative TLC (chloroform-methanol, 10:1). The yield was 8.2 mg (51%). The product was suspended in water (1 mL), and acidified to pH 5 by dropwise addition of 0.05 N hydrochloric acid. The solution was lyophilized to afford the title compound which was stored under nitrogen in a tightly stoppered vessel at −78° C. in the dark. $^1$H NMR (CDCl$_3$) (free base) δ 7.90 (m, 1 H, H1), 7.71 (t, J=8, 1 H, H2), 7.34 (m, 1 H, H3), 5.53–5.10 (m, 5 H, H7, H1", H2"'", H3"'"', H4"'"'), 4.87–4.30 (m, 4 H, H4" (R,S), H1"'"' (R,S), H14), 4.05–3.90 (m, 1 H, H5"'"'), 4.02 (s, 3 H, 4-CH$_3$), 3.75–3.36 (m, 4 H, H4", H5", O$CH_2CH_3$), 3.71 (s, 3 H, $CO_2Me$), 3.25–2.50 (m, 5 H, H10a, H10b, H3", H1"), 2.4–2.2 (m, 2 H, H8a, H8b), 2.04–2.02 (3 s, 9 H, 3 Ac), 2.0–1.5 (m, 6 H, H2", H3", H2"a, H2"b), 1.36 (d, J=6, 3 H, H6"), 1.13–1.05 (m, 3 H, OC$H_2CH_3$).

N-[(4"RS)-4"-Ethoxy-4"-(methyl β-D-glucopyramuronyloxy)butyl]doxorubicin hydrochloride 9b 1 M sodium cyanoborohydride (20 μL, 0.02 mmol) was added to a solution of compound 8b (12 mg, 0.039 mmol) and doxorubicin hydrochloride (22 mg, 0.038 mmol) in acetonitrile-water (2:1) (5 mL) under nitrogen. The mixture was stirred at room temperature in the dark for 2 h. When reaction was complete [as evidenced by TLC of a 5 μL aliquot using chloroform-methanol (9:2) as eluent or HPLC on a C-18 column using 0.05 M ammonium acetate-acetonitrile (6:4) as mobile phase], the solution was diluted with water (8 mL), and then extracted repeatedly (10×10 mL) with chloroform-methanol (5:1). The combined extracts were dried and evaporated to give a red amorphous solid. Preparative TLC of this solid (chloroform-methanol, 7:3) afforded three bands. The fastest moving band was shown by NMR and MS to be the desired product. Yield 16.8 mg (53%). The compound was suspended in water (1 mL), and acidified to pH 5 by dropwise addition of 0.05 N hydrochloric acid. The solution was lyophilized to afford the title compound. $^1$H NMR (CD$_3$OD) (free base) δ 7.86 (m, 1 H, H1), 7.82 (t, 1 H, H2), 7.57 (m, 1 H, H3), 5.49–5.44 (m, 1 H, H1"), 5.07–5.03 (m, 1 H, H7), 4.9–4.2 (m, 4 H, H4" (R,S), H1"'"' (R,S), H14), 4.03 (s, 3 H, 4-CH$_3$), 3.85–3.65 (m, 7 H, H2"'", H3"'"', H4"'"', H5"'"', $CO_2Me$), 3.65–3.15 (m, 4 H, H4", H5", O$CH_2CH_3$), 3.15–2.55 (m, 5 H, H10a, H10b, H3", H1"), 2.4–1.9 (m, 6 H, H8a, H8b, H2"a, H2"b, H3"), 1.8–1.6 (m, 2 H, H2"), 1.30 (d, J=6, 3 H, H6"), 1.18–1.08 (m, 3 H, OC$H_2CH_3$). MS (FAB) m/z 850 (M+H)+.

N-[(4"RS)-4"-Ethoxy-4"-(methyl2"'", 3"'"', 4"'"'-tri-O-acetyl-β-D-glucopyranuroyloxy)]daunorubicin hydrochloride 10a A solution of sodium cyanoborohydride (1 M in tetrahydrofuran; 11.3 μL, 0.0113 mmol) was added to a stirred solution of daunomycin hydrochloride (9.6 mg, 0.017 mmol) and compound 8a (15 mg, 0.035 mmol) in acetonitrile-water (2: 1) (5 mL). The mixture was stirred under a nitrogen atmosphere at room temperature in the dark for 1 h. When reaction was complete, the solution was diluted with water (8 mL), and extracted repeatedly (10×10 mL) with chloroform-methanol (5:1). The product was purified by thick layer chromatography using chloroform-methanol (9:1) as eluent. Yield, 9.0 mg (55%). $^1$H NMR (CDCl$_3$) (free base) δ 8.92 (d, 1 H, J=8, H1), 7.76 (t, J=8, 1 H, H2), 7.37 (d, 1 H, J=8, H3), 5.53 (br. s, 1 H, H1"), 5.35–4.93 (m, 4 H, H2"'", H3"'"', H4"'"', H7), 4.82–4.40 (m, 2 H, H4" (R,S), H1"'"' (R,S)), 4.20–4.0 (m, 1 H, H5"'"'), 4.03 (s, 3 H, 4-CH$_3$), 3.8–3.3 (m, 4 H, H4", H5", O$CH_2CH_3$), 3.69 (s, 3 H, $CO_2Me$), 3.3–2.6 (m, 5 H, H10a, H10b, H3", H1"), 2.40 (s, 3 H, 14-CH$_3$), 2.00–1.98 (3 s, 9 H, 3 Ac), 2.5–1.9 (m, 4 H, H8a, H8b, H3"), 1.9–1.5 (m, 4 H, H2", H2"a, H2"b), 1.32 (d, J=6, 3 H, H6"), 1.19–1.09 (m, 3 H, OC$H_2CH_3$).

N-[(4"RS)-4"-Ethoxy-4"-(β-D-glucopyranuronyloxy)butyl] daunorubicin (Sodium salt) 10b 0.1 N NaOH solution (2.0 mL) was added to a solution of compound 10a (8 mg, 8.0 μmol) in methanol (2.0 mL). The reaction mixture was maintained for 1 h at ambient temperature. It was then added to a column of Amberlite IRC-50 CP cation exchange resin in the H$^+$form (500 mg, 11.3 meq/g). The column was washed with water and the eluent was collected in a flask containing 0.1 M triethylammonium acetate (3 mL, pH 7) that was maintained at 0° C. After all the colored material had eluted, the contents of the flask were frozen and lyophilized. The residual red powder was taken up in water, and the solution was applied to a column of weakly basic cation exchange resin (Biorex 70-Na$^+$; 235 mg). The product was eluted with water. The eluent was frozen and lyophilized to afford the title compound which was characterized by mass spectrometry. Yield, 4.5 mg (67%). MS (FAB, glycerol) m/z 886 [M−2H+3Na]$^+$, 864 [M−H+2Na]$^+$, 842 [M+Na]$^+$, 820 [M+H]$^+$ Example 3

Synthesis of Glucuronide Prodrugs of the Invention

The compounds referred to in this synthesis are shown in FIG. 7. The numbered intermediates of the Figure are cross-referenced in the text below in bold.

Acetal 6 was prepared in two unexceptional steps from alcohol 4, and was reacted with silyl glycoside 3 to give compound 7 using the method described by Tietze, et al. (*Carbohydrate Res.*, Vol. 180 (1988), 253–262). Alkenes such as 7 can be reacted with anthracyclines such as 10 to form the prodrugs following published procedures involving ozonolysis, reductive amination, and deacetylation (A. Cherif, D. Farquhar,. *J. Med Chem.*, Vol. 35 (1992), 3208–3214). The glucuronyl hydroxyls were deprotected before ozonolysis and reductive amination; methanolysis using catalytic NaOMe gave alkene 8 in good yield. Reductive alkylation of the amino group of 10 by aldehyde 9 (obtained by ozonolysis of alkene 8) using NaBH$_4$ or NaBH$_3$CN as a reducing agent gives the prodrug 11. Finally, mild enzymatic hydrolysis of the methyl ester of compound 11 affords prodrug 12. Deesterification can be carried out in vitro, and compound 12 should be stored as the salt of the acid; the acid form is expected to undergo autocatalyzed decomposition. Alternatively, compound 11 can be used as a pre-prodrug, and esterase-catalyzed hydrolysis will occur in vivo.

In detail, the synthesis is as follows:
6,6-Dimethoxy-1-hexene 6

A solution of 5-hexen-1-ol 4 (5.0 g, 50 mmol) in 25 mL of CH$_2$Cl$_2$ was added dropwise to a rapidly stirred suspension of PCC (21.5 g, 100 mmol) in 200 mL of CH$_2$Cl$_2$ cooled by an ice bath. After the addition was complete, the mixture was allowed to warm to room temperature. After 3 h, approximately 20 g of silica gel was added to the dark, tarry mixture, and then the mixture was diluted with 200 mL of ether. Then, the mixture was filtered through a pad of silica gel, eluting with an additional 400 mL of ether. The solvents were removed by distillation to leave 5.7 g of a pale yellow liquid, which contained residual ether, CH$_2$Cl$_2$, 5-hexenyl 5-hexenoate as well as 5-hexenal, compound 5. $^1$H NMR (CDCl$_3$) δ 1.69–1.79 (m, 2, CH$_2$C$\underline{H}_2$CH$_2$), 2.04–2.14 (m, 2, C$\underline{H}_2$CH=CH$_2$), 2.45 (dt, 2, J=1.6, 7.3, C$\underline{H}_2$CHO), 4.97–5.06 (m, 2, CH=C$\underline{H}_2$), 5.77 (dddd, 1, J=6.7, 6.7, 10.2, 17.0, C$\underline{H}$=CH$_2$), 9.77 (t, 1, J=1.6, C$\underline{H}$O); $^{13}$C NMR (CDCl$_3$) δ 21.15, 32.92, 43.07, 115.53, 137.52, 202.46.

The above oxidation can also be carried out using N-methylmorpholine N-oxide (NMO) and catalytic tetrapropylammonium perruthenate (TPAP) in CH$_2$Cl$_2$, moderating the vigorous reaction by cooling with an ice bath.

The crude product containing compound 5 was taken up in 30 mL of MeOH, and camphorsulfonic acid (596 mg, 2.5 mmol) and trimethyl orthoformate (5.46 mL, 50 mmol) were added. The mixture was heated at reflux for 3 h, then allowed to stand at room temperature overnight. The acid was neutralized by the addition of 0.70 mL of triethylamine, and most of the solvent was removed by distillation. The residue was partitioned between water and hexane, the hexane layer was dried over anhydrous Na$_2$SO$_4$, and the solution was filtered through a 3 in column of silica gel, eluting with additional hexane. The solvent was removed by distillation to leave 5.0 g of the product, compound 6, as a colorless liquid. $^1$H NMR (CDCl$_3$) δ 1.39–1.49 (m, 2), 1.58–1.65 (m, 2), 2.03–2.11 (m, 2), 3.31 (s, 6, CH(OC$\underline{H}_3$)$_2$), 4.37 (t, 1, J=5.7C$\underline{H}$(OCH$_3$)$_2$), 4.93–5.05 (m, 2, CH=CH$_2$), 5.80 (dddd, 1, J=6.6, 6.6, 10.3, 16.9, C$\underline{H}$=CH$_2$); $^{13}$C NMR (CDCl$_3$) δ 23.79, 31.83, 33.42, 52.49, 104.33, 114.64, 138.38.

Methyl 2,3,4-tri-O-acetyl-1-O-(R,S-1-methoxy-5-hexenyl)-β-D-glucuronate 7

A 0.1 M solution of trimethylsilyl trifluoromethanesulfonate in CH$_2$Cl$_2$ (0.1 equiv.) was added to a mixture of crude silyl ether 3 (1 equiv., see Example 1 for its preparation) and 1,1-dimethoxy-5-hexene 6 (1 equiv.) in CH$_2$Cl$_2$ (0.1 M) cooled to −78° C. After three days, the trimethylsilyl trifluoromethanesulfonate was neutralized by adding triethylamine (1 equiv.), one volume of ether was added, the solution was warmed to room temperature, filtered through a pad of silica gel with ether, and the filtrate was concentrated in vacuo. Purification by flash chromatography (2% triethylamine in 30–40–70% ethyl acetate/hexane) resulted in the elution of, in order, recovered alkene, α-silyl glucuronide, desilylated glucuronate, and the product 6 as a 2.5:1 mixture of diastereoisomers. $^1$H NMR (CDCl$_3$) δ 1.26–1.37 (m, 2), 1.45–1.57 (m, 2), 1.87–2.00 (m, 11), 3.16 (s, 3, CHOC$\underline{H}_3$ of major isomer), 3.24 (s, 3, CHOC$\underline{H}_3$ of minor isomer), 3.60 (s, 3, COOC$\underline{H}_3$ of minor isomer), 3.60 (s, 3, COOC$\underline{H}_3$ of major isomer), 3.96 (d, 1, J=9.4, H5), 4.45 (t, 1, J=5.5, C$\underline{H}$OCH$_3$ of minor isomer), 4.65 (t, 1, J=5.5, C$\underline{H}$OCH$_3$ of major isomer), 4.65–4.67 (H1 of minor isomer partially obscured), 4.74 (d, 1, J=7.8, H1 of major isomer), 4.78–4.83 (m, 2, CH=CH$_2$), 4.86–4.92 (m, 1, H2), 5.03–5.10 (m, 1, H4), 5.10–5.17 (m, 1, H3), 5.63 (dddd, 1, J=3.0, 9.9, 14.0, 16.8, CH=CH$_2$); $^{13}$C NMR (CDCl$_3$) δ 20.15, 22.98, 23.20, 32.15, 32.91, 32.99, 33.60, 51.74, 52.32, 54.48, 69.12, 70.97, 72.09, 96.12, 102.12, 105.28, 114.41, 138.00, 166.73, 166.82, 168.63, 168.91, 169.62.

Methyl 1-O-(R,S-1-methoxy-5-hexenyl)-β-D-glucuronate 8

To a solution of triacetate 7 (474 mg, 1.06 mmol) in 10 mL of MeOH was added 25 wt % NaOMe in MeOH (0.03 mL). After 1 h, excess ammonium acetate was added to neutralize the mixture. The volatile components were evaporated in vacuo, and the residue was purified by flash chromatography (2% triethylamine in ethyl acetate) to give 304 mg of the product as a colorless oil (89%). R$_f$ 0.28 (2% triethylamine/ethyl acetate); $^1$H NMR (CDCl$_3$) δ 1.39–1.59 (m, 2, H3'), 1.61–1.68 (m, 2, H2'), 2.00–2.07 (m, 2, H4'), 3.23–3.28 (m, 1, H2), 3.34–3.42 (m, 1, H3), 3.37 (s, 3, CHOC$\underline{H}_3$ of major isomer), 3.38 (s, 3, CHOC$\underline{H}_3$ of minor isomer), 3.50–3.57 (m, 1, H4), 3.75 (s, 3, COOC$\underline{H}_3$ of minor isomer), 3.76 (s, 3, COOC$\underline{H}_3$ of major isomer), 3.83 (d, 1, J=9.7, H5 of minor isomer), 3.84 (d, 1, J=9.7, H5 of major isomer), 4.46 (d, 1, J=7.8, H1 of minor isomer), 4.56 (d, 1, J=7.8, H1 of major isomer), 4.56–4.60 (m, 1, C$\underline{\text{H}}$OCH$_3$ of minor isomer), 4.72 (t, 1, J=5.6, C$\underline{\text{H}}$OCH$_3$ of major isomer), 4.90–5.01 (m, 2, CH═C$\underline{\text{H}}_2$), 5.78 (dddd, 1, J=6.7, 6.7, 10.2, 16.9, C$\underline{\text{H}}$═CH$_2$); $^{13}$C NMR (CDCl$_3$) δ 24.59 (C3' major), 24.75 (C3' minor), 34.44 (C4' major), 34.56 (C2' major, C4' minor), 35.36 (C2' minor), 52.78 (COO$\underline{\text{C}}$H$_3$), 53.48 (CHO$\underline{\text{C}}$H$_3$ major), 55.72 (CHO$\underline{\text{C}}$H$_3$ minor), 73.06 (C4), 74.71 (C2 minor), 74.76 (C2 major), 76.74 (C5), 77.34 (C3 major), 77.39 (C3 minor), 100.82 (C1 minor), 101.73 (C1 major), 104.49 (C1' major), 106.99 (C1' minor), 115.02 (C6'), 139.75 (C5'), 171.11 ($\underline{\text{C}}$OOCH$_3$).

Methyl 1-O-(R,S-1-methoxy-5-oxopentyl)-β-D-glucuronate 9

Ozone was bubbled through a solution of alkene 8 (45 mg) in 20 mL of MeOH cooled by a dry ice/acetone bath until a persistent blue color was observed. Excess ozone was purged by bubbling nitrogen through the mixture, and 3 mL of dimethyl sulfide was added to the mixture. After 5 h, the volatile components were evaporated in vacuo. Examination of the residue by $^1$H NMR indicated that the vinyl protons were absent, but no aldehydic protons were observed. The residue was taken up in 10 mL of 1:1 ethyl acetate and CH$_2$Cl$_2$, and 100 mg of anhydrous Na$_2$SO$_4$ and 2 mL of dimethyl sulfide were added. After standing at room temperature for 3 days, the mixture was filtered through a pad of silica gel, eluting further with ethyl acetate. The volatile components were evaporated in vacuo, and examination of the $^1$H NMR spectrum indicated the presence of the aldehydic protons. Partial $^1$H NMR (CDCl$_3$) d 1.61–1.71 (m, 4, C$\underline{\text{H}}_2$CH$_2$C$\underline{\text{H}}_2$CHO), 2.41 (C$\underline{\text{H}}_2$CHO of major isomer), 2.56 (C$\underline{\text{H}}_2$CHO of minor isomer), 3.38 (s, 3, CHOC$\underline{\text{H}}_3$ of major isomer), 3.45–3.50 (m, 1, H2), 3.58–3.64 (m, 1, H3), 3.71–3.77 (m, 1, H4), 3.79 (s, 3, COOC$\underline{\text{H}}_3$ of minor isomer), 3.80 (s, 3, COOC$\underline{\text{H}}_3$ of major isomer), 3.90 (d, 1, J=9.6, H5), 4.52 (d, 1, J=7.8, H1 of minor isomer), 4.60 (d, 1, J=7.7, H1 of major isomer), 4.75 (bs, 1, C$\underline{\text{H}}$OCH$_3$ of major isomer), 9.74 (s, 1, C$\underline{\text{H}}$═O of major isomer), 9.77 (s, 1, C$\underline{\text{H}}$═O of minor isomer).

Reductive alkylation of doxorubicin 10 by aldehyde 9

Solid NaBH$_4$ (0.7 equiv.) is added to a 0.01 M solution of doxorubicin hydrochloride 10 in 2:1 MeOH/H20 containing aldehyde 9 (2 equiv.). The mixture is stirred in the dark under argon at room temperature until the starting material is consumed as observed by TLC. The solution is diluted with 1.5 volumes of H$_2$O and extracted repeatedly with 5:1 CHCl$_3$/MeOH. The organic phases are dried over anhydrous Na$_2$SO$_4$ and concentrated in vacuo. The product, compound 11, is purified by reverse phase HPLC (125 mM Et$_3$N-HOAc in H2O (pH 7)/MeOH), repeated lyophilization to remove excess buffer salts, and ion exchange on DEAE-Sepharose (HCl form).

Hydrolysis of compound 11 to give compound 12

Pig liver esterase (130 U) is added to a 0.1 M solution of ester 11 in 0.1 M sodium phosphate buffer (pH 7.5) at 33° C. After 5 h, the mixture is filtered through a membrane filter, and the product 12 is purified from the filtrate chromatographically.

Example 4

Prodrug Enzyme Activation

Enzymes. β-Glucuronidase (*E. Coli*) (EC 3. 2. 1. 31) was purchased from Sigma Chemical Co., St. Louis, Mo. and was used as received. The specific activity of the preparation was 16,000 units/mg protein, where 1 unit is defined as the amount of enzyme that will liberate 1.0 µg of phenolphthalein from phenolphthalein β-glucuronide per hour at pH 6.8 and 37° C.

Stability Studies of N-[(4"RS)-4"-Ethoxy-4"-(B-D-glucopyranurongloxy)butyl] daunorubicin (sodium salt) 10b in the Presence of β-glucuronidase.

The title compound (in the form of its sodium salt) (16.8 µg; 0.02 µmol) was dissolved in 0.05 M potassium phosphate buffer, pH 7.4 (200 µL) contained in a 2.0-mL glass vial (final drug concentration 10$^{-4}$M). The solution was incubated at 37° C. for 50 h. At selected time intervals (1, 4, 8, 12, 24, 30, and 50 h) aliquots (10 µL) were withdrawn and analyzed for parent drug by HPLC on a C-18 reverse-phase column (Waters Associates, Milford, Mass.; µ-Bondapak C-18; 200×4.6 mm, i.d.). A solution of CH$_3$CN-0.05M acetate buffer, pH 4.0 (2:3; v/v), at a flow rate of 1.0 mL/min, was used as mobile phase. (retention time=3.91 min).

For the enzyme studies, 10b (33.6 µg; 0.04 µmol) and sodium cyanide (9.8 pg; 0.2 µmol) were dissolved in 0.05 M potassium phosphate buffer, pH 7.4 (380 µL) contained in a 2.0-mL glass vial (final drug concentration 10$^{-4}$M). The reaction was initiated by the addition of 28 units of β-glucuronidase (2.2 units of enzyme per tmole of substrate) in the same buffer (20 µL). At intervals of 0.25, 0.5, 2, 5, 8, 24, and 32 h, aliquots (20 µL) of the mixture were withdrawn and added to 4 volumes of MeOH contained in 1.5-mL centrifuge tubes. The tubes were agitated on a Vortex shaker for 20 s and then centrifuged for 4 min at 1000 rpm. Aliquots (25 µL) of the clear supernatant were analyzed by UPLC as described above. The peak corresponding to the parent compound gradually disappeared and was replaced by two peaks with retention times of 6.58 and 7.08, respectively. The experiment was repeated in the presence of 10 units and 20 units of the enzyme per umol of substrate. The half-lives for the disappearance of 10b, determined by linear least-square regression analysis of the pseudo first-order reactions were:

2-fold enzyme excess, 8.1 h; 10-fold enzyme excess, 6.9 h; 20-fold enzyme excess, 2.0 h.

Growth Inhibition Studies. Six cell lines: A-375 (human melanoma), LSl174T (colon carcinoma), ME 180 (cervical carcinoma), SK-OV-3 (ovarian carcinoma), and BT-474 (breast carcinoma) were routinely grown in Hank's Minimal Essential Medium (MEM, Gibco Inc.) containing 10% fetal bovine serum albumin (Atlanta Biologics). Cells were passaged weekly by trypsinization (Gibco) followed by plating at reduced density (50,000 cells/ml). They were routinely tested and found to be free of mycoplasma contamination. Cells were harvested by trypsinization and plated in 96 well plates at a density of 5,000 per well in 100 µl of MEM culture media. Cells were allowed to adhere by incubation for 24 hr at 37° C. in humidified 5% CO$_2$. The wells containing log-phase cells were treated with complete MEM containing serial dilutions of N-[(4"RS-4"-Ethoxy-4"-β-D-glucopyranurongloxy)butyl]daunorubicin (sodium salt) 10b at concentrations ranging from 10$^{-5}$ to 10$^{-14}$M Each well also contained a 50-fold unit excess of β-glucuronidase (i.e., 50 units of enzyme per βmole of substrate). Control reactions were run with 10b in the absence of β-glucuronidase, daunomycin alone, and daunomycin in the presence β-glucuronidase. The cells were then incubated for a further 72 hr at 37° C. in a humidified CO$_2$ incubator. The wells were emptied and the remaining cells were stained by the addition of 100 µl of 0.5% Crystal Violet (Fischer Scientific) in 20% methanol (Fischer Scientific). After incubation for 20 min, the dye was removed, and the wells were washed were with deionized water. Cell-bound dye was solubilized with Sorenson's Buffer (0.1 M sodium citrate, pH 4.2-ethanol, 1:1, v/v) and the wells were read on an ELISA microplate autoreader at 540 nm. Dose-response curves were constructed and the $IC_{50}$ values (the drug concentrations that inhibited cell growth by 50%) determined.

With the A375 cell line the IC50 for the glucuronide was $2\times10^{-7}$ g ml. In the presence of glucuronidase, the IC50 was $2\times10^{-11}$ g ml. demonstrating the potency of these compounds as prodrugs on specific activation.

Example 5

Endogenous Enzyme Activation of Prodrugs in Animal Models

The studies in animals followed protocols similar to those seen with the cell lines used for in vivo studies are colon carcinoma cell lines LS174T (ATCC CL 188), Colo 205 (ATCC CCL 222), Lovo (ATCC CCL 229), Cx1, Mx1, B16, CU38, and H. Tumor cells were implanted as sub-cutaneous injection of $3\times10^6$ for LS174T and allowed to grow to desired size typically a tumor volume of 20–100 mm ($L\times W^2/2$) in about 4–8 days from sub-cutaneous injection of the tumor cell lines into the nude mice (NCr nude mice female 6–9 week, Taconic Farms Inc. or Jackson Labs). The Cx1, and Mx1 tumors were transplanted by insertion of 1–10 $mm^3$ subcutaneously. The mouse tumors LL (lewis lung) and Cu38 colon C-38 were carried in BDF1 mice. The tumor volumes were calculated based on caliper measurements. In any given study there are 10 animals in the control group and 5–10 in the treatment groups. Animals were treated with prodrug in the range of 0.5–50 mg/kg/day with treatment schedules from 3 to 12 days of consecutive IV treatments.

α Tumor size was monitored also at 2–4 day intervals. In a parallel set of animals, the pH of the tumor was also modified by the use of IP injections of D-glucose (4.5 mg/g) and Na $HCO_3$(0.33mg/g) these were then dosed with prodrug after 40 min with 0.5–50 mg/kg/day. This cycle of glucose/$NaHCO_3$ followed by prodrug would be repeated daily for 3–12 days of treatment as in the prodrug only group.

The animals in the study after final prodrug treatment were monitored for up to 60 days. The results demonstrated significant reduction of tumor growth for treated animals. At the end of the experiment the tumor mass was also measured by excision of the tumor mass.

Example 6

Exogenous Enzyme Activation of Prodrugs in Animal Models

The studies in animals basically followed those of Meyer D L et al (Cancer Res 1993 53, 3956–3963). The cell lines used for the in vivo studies were colon carcinoma cell lines LSl174T (ATCC CL 188), Colo 205 (ATCC CCL 222) and Lovo (ATCC CCL 229). Tumor cells were implanted as sub-cutaneous injection of $3\times10^6$ for LS174T and allowed to grow to the desired size typically a tumor volume of 20–100 $mm^3$($L\times W/2$) in about 4–8 days from sub-cutaneous injection of the tumor cell lines into the nude mice (NCr nude mice female 6–9 week, Taconic Farms Inc. or Jackson Labs). The tumor volumes were calculated based on caliper measurements. In any given study, there were 10 animals in the control group, and 5–10 in the treatment group. Animals were treated enzyme doses at 35–500 µg per mouse some with repeated doses of up to three separate treatments. Typically, enzyme was dosed at day 4–81, with a time interval of 4–12 days between the enzyme doses. The prodrug treatment was normally applied at 3–10 days after the enzyme injection. Prodrug doses were in the range of 0.5–50 mg/kg/day.

Tumor size was monitored also at 2–4 day intervals. In a parallel set of animals, the pH of the tumor was also modified by the use of IP injections of D-glucose (4.5 mg/g) and Na $HCO_3$(0.33 mg/g) these were then dosed with prodrug after 40 min with 0.5–50 mg/kg/day. This cycle of glucose/$NaHCO_3$ followed by prodrug was repeated daily for 3–10 days of treatment. The animals in the study were monitored for up to 60 days at 7 day intervals.

The results demonstrated significant reduction of tumor growth for animals treated with the enzyme followed by prodrug both with pH modulation by the glucose infusion protocol. At the end of the experiment the tumor mass was also measured by excision of the tumor mass.

Example 7

Targeted Antibody-Enzyme Activation of Prodrugs in Animal Models

The studies in animals basically followed those of Meyer D L et al (Cancer Res 1993 53, 3956–3963). The cell lines used for in vivo studies were colon carcinoma cell lines LS 174T (ATCC CL 188), Colo 205 (ATCC CCL 222) and Lovo (ATCC CCL 229). Tumor cells were implanted by sub-cutaneous injection of $3\times10^6$ for LS174T and allowed to grow to the desired size, typically, a tumor volume of 20–100 mm ($L\times W^2/2$) in about 4–8 days from sub-cutaneous injection of the tumor cell lines into the nude mice (NCr nude mice female 6–9 week, Taconic Farms Inc. or Jackson Labs.) The tumor volumes were calculated based on caliper measurements. In any given study 10 animals were the control group, and 5 in treatment group. Animals were treated with specific (anti-TAG-72, anti CEA antibody fusions) and also non-specific (anti NP antibody fusion) at various time points with antibody-enzyme doses at 35–280 µg per mouse some with repeated doses up to three separate treatments. Typically, antibody was dosed at day 4–81, with a time interval of 4–12 days between the antibody doses. The prodrug treatment was normally applied at 3–10 days after the antibody injection. Prodrug doses were in the range of 0.5–50 mg/kg/day.

Tumor size was monitored also at 2 day intervals. In a parallel set of animals the pH of the tumor was also modified by the use of IP injections of D-glucose (4.5 mg/g) and Na $HCO_3$(0.33 mg/g) these were then dosed with prodrug after 40 min with 0.5–50 mg/kg/day. This cycle of glucose/$NaHCO_3$ followed by prodrug was repeated daily for 3–10 days of treatment.

The animals in the study were monitored for up to 60 days at 7 day intervals. The results demonstrated significant reduction of tumor growth for animals treated with the specific antibody followed by prodrug both with and without pH modulation by the glucose infusion protocol. At the end of the experiment the tumor mass was also measured by excision of the tumor mass.

The foregoing is intended as illustrative of the present invention but not limiting. Numerous variations and modifications may be effected without departing from the true spirit and scope of the invention.

What is claimed is:

1. A compound of the formula

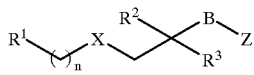

where:
- $R^1$ is a radical of an anthracyclinone where the point of attachment is the 3' nitrogen of the daunosamine sugar;
- $R^2$ is H, alkyl having from 1 to 6 carbon atoms, aromatic having from 6 to 10 carbon atoms or heteroaromatic having from 5 to 8 atoms in the heteroaromatic ring substituted with $NO_2$, CN, F, Cl, OH, alkoxy having from 1 to 6 carbon atoms, COMe, $CF_3$, COOH, COO alkyl having from 1 to 10 carbon atoms or COO aryl having from 6 to 10 carbon atoms;
- $R^3$ is cyano, methoxy, ethoxy, alkoxy having from 3 to 18 carbon atoms, or aryloxy having from 6 to 10 carbon atoms substituted with $NO_2$, CN, F, Cl, OH, alkoxy having from 1 to 6 carbon atoms, COMe, $CF_3$, COOH, or COO alkyl having from 1 to 10 carbon atoms or COO aryl having from 6 to 10 carbon atoms, acetoxy, propionyloxy, trimethylacetoxy, or benzoyloxy;
- $X=CH_2$, O, S, or N substituted by H, alkyl or acyl having from 1 to 6 carbon atoms, aromatic having from 6 to 10 carbon atoms or heteroaromatic having from 5 to 8 carbon atoms in the heteroaromatic ring substituted with methyl, ethyl, acetyl or benzoyl;
- n=2 if X=O, S, or substituted N;
- n=1 or 2 if $X=CH_2$;
- B is O, NHCOO, or one of the following substituted aromatics:

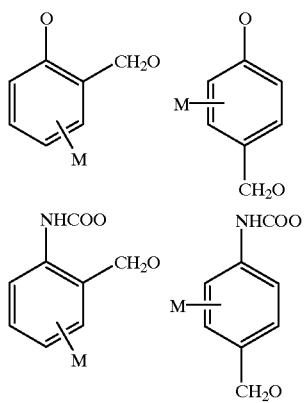

wherein from 1–4 Ms are substituted on the ring and where M is H, $NO_2$, CN, F, Cl, OH, alkoxy having from 1 to 18 carbon atoms in the heteroaromatic ring, COMe, $CF_3$, COOH, COO alkyl having from 1 to 10 carbon atoms or COO aryl having from 6 to 10 carbon atoms, aromatic having from 6 to 10 carbon atoms or heteroaromatic having from 5 to 8 atoms in the heteroaromatic ring, methyl or alkyl having from 2 to 18 carbon atoms; and
- Z is a glycosyl, or substituted aliphatic acyl having from 1 to 18 carbon atoms or aromatic acyl having from 6–10 carbon atoms, attached to the aromatic or carbamoyl O of B at the anomeric carbon of Z;
- provided that where $R^3$ is aryloxy, acetoxy, propionyloxy, trimethylacetoxy, or benzoyloxy, BZ cannot be the same as $R^3$.

2. A compound as in claim 1 wherein said anthracyclinone is doxorubicin or daunorubicin.

3. A compound as in claim 1 wherein Z is a galactosyl, glucuronyl, salt of glucuronyl or ester of glucuronyl having 1 to 4 carbon atoms.

4. A compound as in claim 1 wherein $R^2$ is a phenyl, thiophenyl, or pyridinyl substituted with $NO_2$, F, OMe, or $CF_3$.

5. A compound as in claim 1 wherein $R^3$ is an aryloxy substituted with $NO_2$, F, OMe, or $CF_3$.

6. A compound as in claim 1 wherein X is an O or an N substituted with a methyl, ethyl, or phenyl.

7. A compound as in claim 1 wherein M is alkoxy having from 1–3 carbon atoms, COO alkyl having from 1–3 carbon atoms or alkyl having from 1–3 carbon atoms.

8. A compound as in claim 1 wherein one M is substituted on the ring.

9. A compound as in claim 1 wherein Z is an aliphatic alkyl or acyl having from 1–7 carbon atoms or an aromatic acyl having from 6–10 carbon atoms.

10. A compound as in claim 1 having the formula

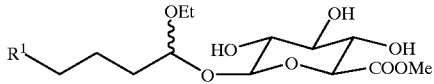

wherein $R^1$ is a radical of daunorubicin or doxorubicin where the point of attachment is the 3' nitrogen of the daunosamine sugar.

11. A compound as in claim 1 having the formula

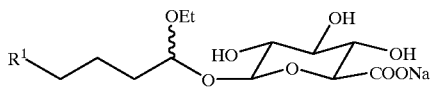

wherein $R^1$ is a radical of daunorubicin or doxorubicin where the point of attachment is the 3' nitrogen of the daunosamine sugar.

12. A compound as in claim 1 having the formula

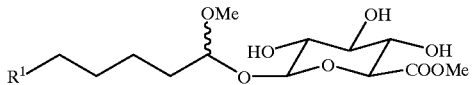

wherein $R^1$ is a radical of daunorubicin or doxorubicin where the point of attachment is the 3' nitrogen of the daunosamine sugar.

13. A compound as in claim 1 having the formula

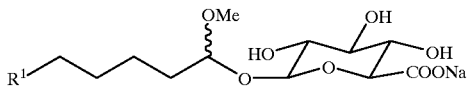

wherein $R^1$ is a radical of daunorubicin or doxorubicin where the point of attachment is the 3' nitrogen of the daunosamine sugar.

14. A compound as in claim 1 having the formula

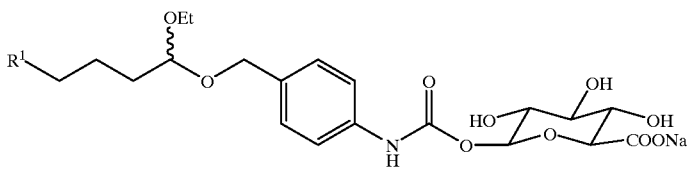

wherein $R^1$ is a radical of daunorubicin or doxorubicin where the point of attachment is the 3' nitrogen of the daunosamine sugar.

15. A compound as in claim 1 having the formula

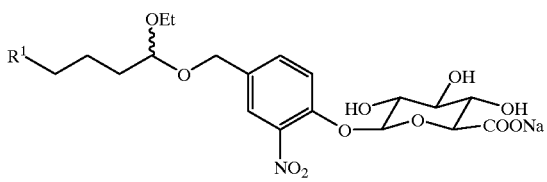

wherein $R^1$ is a radical of daunorubicin or doxorubicin where the point of attachment is the 3' nitrogen of the daunosamine sugar.

16. A compound as in claim 1 wherein M is phenyl.

17. A compound as in claim 1 wherein $R^3$ is phenyloxy.

18. A compound as in claim 1 wherein $R^2$ is OMe.

19. A compound of the formula

where $R^1$ is a radical of an anthracyclinone where the point of attachment is the 3' nitrogen of the daunosamine sugar;

n=1 or 2;

$R^2$ is H, alkyl having from 1 to 6 carbon atoms, aromatic having 6–10 carbon atoms or heteroaromatic having from 5 to 8 atoms in the heteroaromatic ring substituted with $NO_2$, CN, F, Cl, OH, alkoxy having from 1 to 6 carbon atoms, COMe, $CF_3$, COOH, COO alkyl having 1–10 carbon atoms or COO aryl having from 6 to 10 carbon atoms;

B is O, NHCOO, or one of the following substituted aromatics:

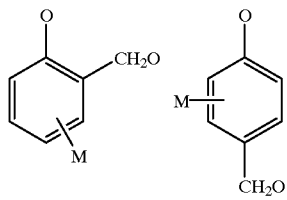

-continued

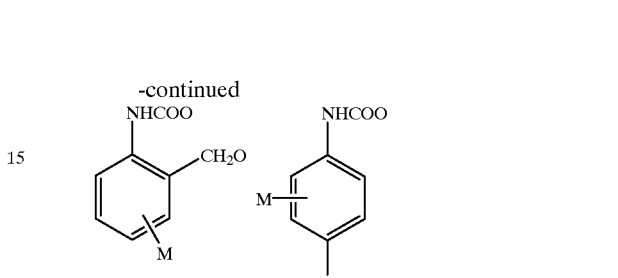

where M is H, $NO_2$, CN, F, Cl, OH, alkoxy having from 1 to 18 carbon atoms, COMe, $CF_3$, COOH, COO alkyl having 1–10 carbon atoms or COO aryl having from 6 to 10 carbon atoms, aromatic having 6–10 carbon atoms or heteroaromatic having from 5 to 8 atoms in the heteroaromatic ring, methyl or alkyl having from 2 to 18 carbon atoms; and Z is a glycosyl, or substituted aliphatic acyl having 1–10 carbon atoms or aromatic acyl having from 6 to 10 carbon atoms, attached to the aromatic or carbamoyl O of B at the anomeric carbon of Z.

20. A compound as in claim 19 wherein Z is a galactosyl, glucuronyl, salt of glucuronyl or ester of glucuronyl having 1 to 4 carbon atoms.

21. A compound as in claim 19 having the formula

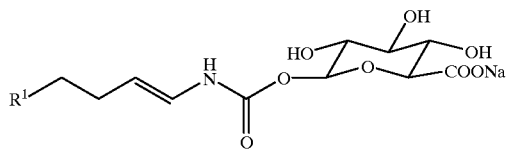

wherein $R^1$ is a radical of daunorubicin or doxorubicin where the point of attachment is the 3' nitrogen of the daunosamine sugar.

22. A compound of the formula

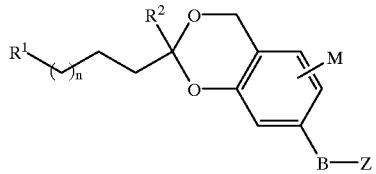

where:

B is O or NHCOO;

$R^1$ is a radical of an anthracyclinone where the point of attachment is the 3' nitrogen of the daunosamine sugar;

n=1 or 2;

$R^2$ is H, alkyl having from 1 to 6 carbon atoms, aromatic having 6–10 carbon atoms or heteroaromatic having from 5 to 8 carbon atoms in the heteroaromatic ring substituted with $NO_2$, CN, F, Cl, OH, or alkoxy having from 1 to 6 carbon atoms, COMe, $CF_3$, COOH, COO alkyl having 1–10 carbon atoms or COO aryl having from 6 to 10 carbon atoms;

M is $NO_2$, CN, F, Cl, OH, alkoxy having from 1 to 18 carbon atoms, COMe, $CF_3$, COOH, COO alkyl having 1–10 carbon atoms or COO aryl having from 6 to 10 carbon atoms, aromatic having 6–10 carbon atoms or heteroaromatic having from 5 to 8 atoms in the heteroaromatic ring, methyl or alkyl having from 2 to 18 carbon atoms; and Z is a glycosyl, or substituted aliphatic acyl having from 1 to 18 carbon atoms or aromatic acyl having 6–10 carbon atoms, attached to the carbamoyl O of B at the anomeric carbon of Z.

23. A compound as in claim 22 wherein Z is a galactosyl, glucuronyl, salt of glucuronyl or ester of glucuronyl having 1 to 4 carbon atoms.

24. A compound as in claim 22 having the formula

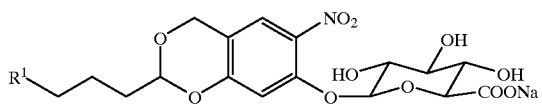

wherein $R^1$ is a radical of daunorubicin or doxorubicin where the point of attachment is the 3' nitrogen of the daunosamine sugar.

25. A compound of the formula

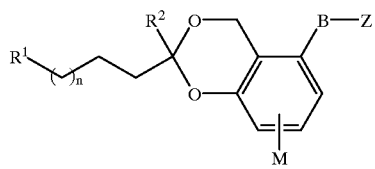

where $R^1$ is a radical of an anthracyclinone where the point of attachment is the 3' nitrogen of the daunosamine sugar;

n=1 or 2;

$R^2$ is H, alkyl having from 1 to 6 carbon atoms, aromatic having 6–10 carbon atoms or heteroaromatic having from 5 to 8 atoms in the heteroaromatic ring substituted with $NO_2$, CN, F, Cl, OH, alkoxy having from 1 to 6 carbon atoms, COMe, $CF_3$, COOH, COO alkyl having 1–10 carbon atoms or COO aryl having from 6 to 10 carbon atoms;

B is O or NHCOO;

M is H, $NO_2$, CN, F, Cl, OH, alkoxy having from 1 to 18 carbon atoms, COMe, $CF_3$, COOH, COO alkyl having from 1 to 10 carbon atoms, COO aryl having from 6 to 10 carbon atoms, aromatic having 6–10 carbon atoms, heteroaromatic having from 5 to 8 atoms in the heteroaromatic ring, methyl or alkyl having from 2 to 18 carbon atoms; and Z is a glycosyl, or substituted aliphatic acyl having from 1 to 18 carbon atoms or aromatic acyl having 6–10 carbon atoms, attached to the carbamoyl O of B at the anomeric carbon of Z.

26. A compound as in claim 25 wherein Z is a galactosyl, glucuronyl, salt of glucuronyl or ester of glucuronyl having 1 to 4 carbon atoms.

27. A compound of the formula

where:

$R^1$ is a radical of an anthracyclinone where the point of attachment is the 3' nitrogen of the daunosamine sugar;

n=2 or 3;

B is COO or one of the following aromatics:

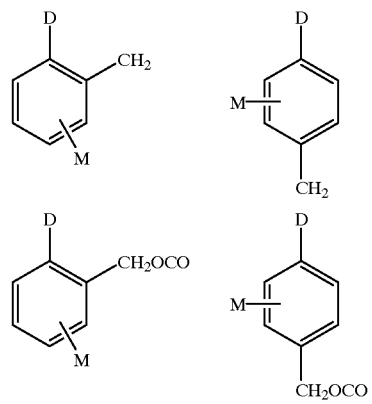

where B is attached to $R^1$ via the $CH_2$ or $CH_2OCO$ of B; and D is attached to Z, and D is O or NHCOO where Z is attached at the carbamoyl O;

M is $NO_2$, CN, F, Cl, OH, alkoxy having from 1 to 18 carbon atoms, COMe, $CF_3$, COOH, COO alkyl having 1–10 carbon atoms or COO aryl having from 6 to 10 carbon atoms, aromatic having 6–10 carbon atoms, heteroaromatic having from 5 to 8 atoms in the heteroaromatic ring, methyl or alkyl having from 2 to 18 carbon atoms;

Z is a glycosyl, or substituted aliphatic acyl having from 1 to 18 carbon atoms or aromatic acyl having 6–10 carbon atoms, attached to the O of D at the anomeric carbon of Z; and L is a latent aldehyde or methyl ketone.

28. A compound as in claim 27 wherein Z is a galactosyl, glucuronyl, salt of glucuronyl or ester of glucuronyl having 1 to 4 carbon atoms.

29. A compound as in claim 27 having the formula

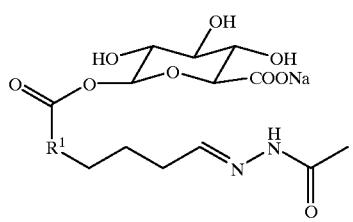

wherein $R^1$ is a radical of daunorubicin or doxorubicin where the point of attachment is the 3' nitrogen of the daunosamine sugar.

30. A compound as in claim 27 having the formula

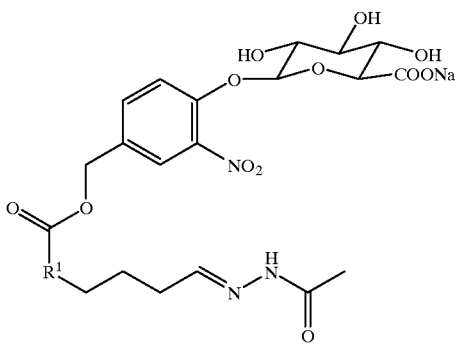

wherein $R^1$ is a radical of daunorubicin or doxorubicin where the point of attachment is the 3' nitrogen of the daunosamine sugar.

31. A compound of the formula

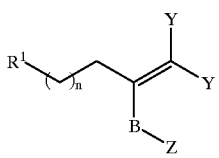

where:
  Y=F, Cl or Br;
  $R^1$ is a radical of an anthracyclinone where the point of attachment is the 3' nitrogen of the daunosamine sugar;
  n=1 or 2;
  B is O, NHCOO, or one of the following substituted aromatics:

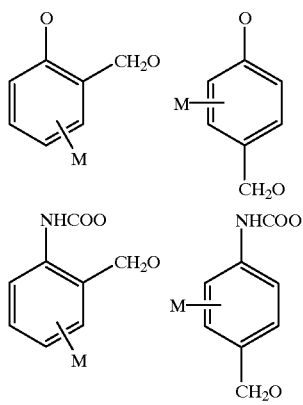

where M is H, $NO_2$, CN, F, Cl, OH, alkoxy having from 1 to 18 carbon atoms, COMe, $CF_3$, COOH, COO alkyl having 1–10 carbon atoms or COO aryl having from 6 to 10 carbon atoms, aromatic having 6–10 carbon atoms or heteroaromatic having from 5 to 8 carbon atoms in the heteroaromatic ring, methyl or alkyl having from 2 to 18 carbon atoms; and Z is a glycosyl, or substituted aliphatic acyl having from 1 to 18 carbon atoms or aromatic acyl having 6–10 carbon atoms, attached to the aromatic or carbamoyl O of B at the anomeric carbon of Z.

32. A compound as in claim 31 wherein Z is a galactosyl, glucuronyl, salt of glucuronyl or ester of glucuronyl having 1 to 4 carbon atoms.

33. A compound of the formula

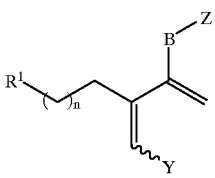

where:
  Y=F, Cl or Br;
  $R^1$ is a radical of an anthracyclinone where the point of attachment is the 3' nitrogen of the daunosamine sugar;
  n=1 or 2;
  B is O, NHCOO, or one of the following substituted aromatics:

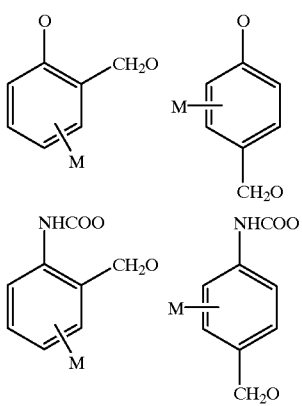

where M is H, $NO_2$, CN, F, Cl, OH, alkoxy having from 1 to 18 carbon atoms, COMe, $CF_3$, COOH, COO alkyl having 1–10 carbon atoms or COO aryl having from 6 to 10 carbon atoms, aromatic having 6–10 carbon atoms or heteroaromatic having from 5 to 8 carbon atoms in the heteroaromatic ring, methyl or alkyl having from 2 to 18 carbon atoms; and Z is a glycosyl, or substituted aliphatic acyl having from 1 to 18 carbon atoms or aromatic acyl having 6–10 carbon atoms, attached to the aromatic or carbamoyl O of B at the anomeric carbon of Z.

34. A compound as in claim 33 wherein Z is a galactosyl, glucuronyl, salt of glucuronyl or ester of glucuronyl having 1 to 4 carbon atoms.

35. A compound of the formula

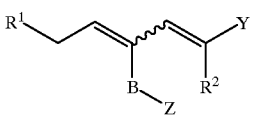

where:
  Y=F, Cl, Br;
  $R^1$ is a radical of an anthracyclinone where the point of attachment is the 3' nitrogen of the daunosamine sugar;
  $R^2$ is H, alkyl having from 1 to 6 carbon atoms, aromatic having 6–10 carbon atoms or heteroaromatic having from 5 to 8 atoms in the heteroaromatic ring substituted with $NO_2$, CN, F, Cl, OH, or alkoxy having from 1 to 6 carbon atoms, COMe, $CF_3$, COOH, COO alkyl having 1–10 carbon atoms or COO aryl having from 6 to 10 carbon atoms;

B is O, NHCOO, or one of the following substituted aromatics:

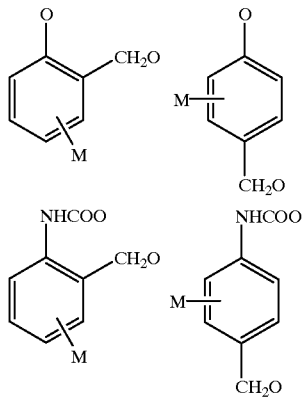

where M is H, NO$_2$, CN, F, Cl, OH, alkoxy having from 1 to 18 carbon atoms, COMe, CF$_3$, COOH, COO alkyl having 1–10 carbon atoms or COO aryl having from 6 to 10 carbon atoms, aromatic having 6–10 carbon atoms or heteroaromatic having from 5 to 8 carbon in the heteroaromatic ring, methyl or alkyl having from 2 to 18 carbon atoms; and Z is a glycosyl, or substituted aliphatic acyl having from 1 to 18 carbon atoms or aromatic acyl having 6–10 carbon atoms, attached to the aromatic or carbamoyl O of B at the anomeric carbon of Z.

36. A compound as in claim 35 wherein Z is a galactosyl, glucuronyl, salt of glucuronyl or ester of glucuronyl having 1 to 4 carbon atoms.

37. A compound of the formula

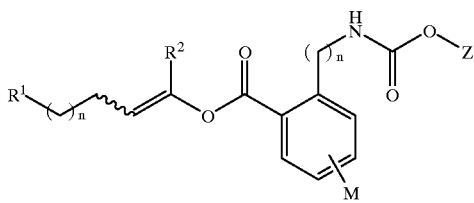

where:
R$^1$ is a radical of an anthracyclinone where the point of attachment is the 3' nitrogen of the daunosamine sugar;
R$^2$ is H, alkyl having from 1 to 6 carbon atoms, aromatic having 6–10 carbon atoms or heteroaromatic having from 5 to 8 atoms in the heteroaromatic ring substituted with NO$_2$, CN, F, Cl, OH, or alkoxy having from 1 to 6 carbon atoms, COMe, CF$_3$, COOH, COO alkyl having 1–10 carbon atoms or COO aryl having from 6 to 10 carbon atoms;
n=1 or 2;
M is H, NO$_2$, CN, F, Cl, OH, alkoxy having from 1 to 18 carbon atoms, COMe, CF$_3$, COOH, COO alkyl having 1–10 carbon atoms or COO aryl having from 6 to 10 carbon atoms, aromatic having 6–10 carbon atoms or heteroaromatic having from 5 to 8 atoms in the heteroaromatic ring, methyl or alkyl having from 2 to 18 carbon atoms; and
Z is a glycosyl.

38. A compound as in claim 37 wherein Z is a galactosyl, glucuronyl, salt of glucuronyl or ester of glucuronyl having 1 to 4 carbon atoms.

39. A compound of the formula

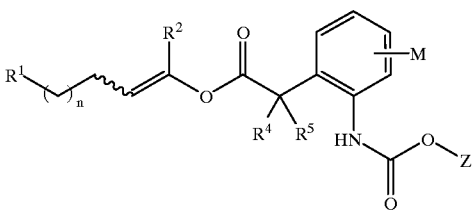

where:
R$^4$ and R$^5$ are the same or different and are alkyl, aryl having 6–10 carbon atoms, or heteroaromatic having from 5 to 8 atoms in the heteroaromatic ring;
R$^1$ is a radical of an anthracyclinone where the point of attachment is the 3' nitrogen of the daunosamine sugar;
R$^2$ is H, alkyl having from 1 to 6 carbon atoms, aromatic having 6–10 carbon atoms or heteroaromatic having from 5 to 8 atoms in the heteroaromatic ring substituted with NO$_2$, CN, F, Cl, OH, or alkoxy having from 1 to 6 carbon atoms, COMe, CF$_3$, COOH, COO alkyl having 1–10 carbon atoms or COO aryl having from 6 to 10 carbon atoms;
n=1 or 2;
M is H, NO$_2$, CN, F, Cl, OH, alkoxy having from 1 to 18 carbon atoms, COMe, CF$_3$, COOH, COO alkyl having 1–10 carbon atoms or COO aryl having from 6 to 10 carbon atoms, aromatic having 6–10 carbon atoms or heteroaromatic having from 5 to 8 carbon atoms in the heteroaromatic ring, methyl or alkyl having from 2 to 18 carbon atoms; and
Z is a glycosyl.

40. A compound as in claim 39 wherein Z is a galactosyl, glucuronyl, salt of glucuronyl or ester of glucuronyl having 1 to 4 carbon atoms.

41. A compound of the formula

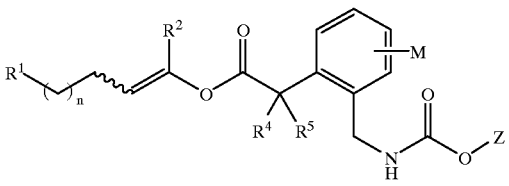

where:
R$^1$ is a radical of an anthracyclinone where the point of attachment is the 3' nitrogen of the daunosamine sugar;
R$^2$ is H, alkyl having from 1 to 6 carbon atoms, aromatic having 6–10 carbon atoms or heteroaromatic having from 5 to 8 atoms in the heteroaromatic ring substituted with NO$_2$, CN, F, Cl, OH, or alkoxy having from 1 to 6 carbon atoms, COMe, CF$_3$, COOH, COO alkyl having 1–10 carbon atoms or COO aryl having from 6 to 10 carbon atoms;
R$^4$ and R$^5$ are the same or different and are alkyl, aryl having 6–10 carbon atoms, or heteroaromatic having from 5 to 8 atoms in the heteroaromatic ring;
n=1 or 2;
M is H, NO$_2$, CN, F, Cl, OH, alkoxy having from 1 to 18 carbon atoms, COMe, CF$_3$, COOH, COO alkyl having 1–10 carbon atoms or COO aryl having from 6 to 10 carbon atoms, aromatic having 6–10 carbon atoms or heteroaromatic having from 5 to 8 atoms in the heteroaromatic ring, methyl or alkyl having from 2 to 18 carbon atoms; and Z is a glycosyl.

42. A compound as in claim 41 wherein Z is a galactosyl, glucuronyl, salt of glucuronyl or ester of glucuronyl having 1 to 4 carbon atoms.

43. A compound having the formula

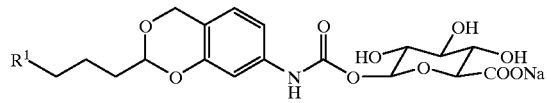

wherein $R^1$ is a radical of daunorubicin or doxorubicin where the point of attachment is the 3' nitrogen of the daunosamine sugar.

44. A compound as having the formula

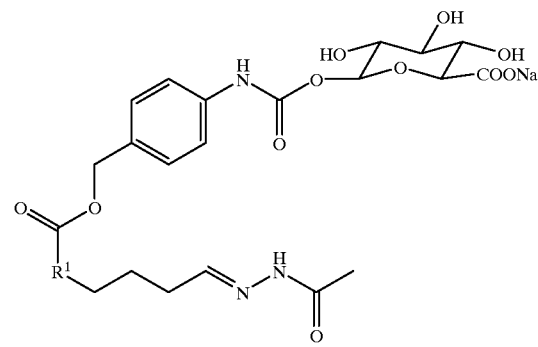

wherein $R^1$ is a radical of daunorubicin or doxorubicin where the point of attachment is the 3' nitrogen of the daunosamine sugar.

* * * * *